United States Patent [19]

DeVries et al.

[11] Patent Number: 4,943,629

[45] Date of Patent: Jul. 24, 1990

[54] ANTIDIABETIC ALPHA-SUBSTITUTED PHOSPHONATES

[75] Inventors: Vern G. DeVries, Ridgewood; Thomas H. Claus, Montvale, both of N.J.; Middleton B. Floyd, Jr., Suffern; Semiramis Ayral-Kaloustian, Tarrytown, both of N.Y.

[73] Assignee: American Cyanamid Company, Stamford, Conn.

[21] Appl. No.: 232,331

[22] Filed: Aug. 12, 1988

[51] Int. Cl.$^5$ .............................................. C07H 11/04
[52] U.S. Cl. .................................................... 536/117
[58] Field of Search ....................... 536/117; 514/24, 25

[56] References Cited

U.S. PATENT DOCUMENTS 4,745,185 5/1988 Maryanoff et al. .................. 536/117

OTHER PUBLICATIONS

The British Drug Houses Ltd., "Sugar Phosphates and some Closely Related Substances", Mar. 1958, p. 5.
Rabinsohn et al., J. Org. Chem., 32, 3452-3457 (1967).
Koerner et al., Carbohydrate Res., 59, 403-416 (1977).
Pilkis et al., J. Biol. Chem., 256, 3171-3174 (1981).
Voll et al., Carbohydrate Res., 95, 145-154 (1981).
Otero et al., Carbohydrate Res., 128, 79-86 (1984).
McClard et al., Arch. Biochem. & Biophys., 245, 282-286 (1986).
Meuwly, Helv. Chim. Acta, 69, 751-760 (1986).
Nicotra et al., J. Org. Chem., 52, 5627-5630 (1987).
Reitz et al., Tetrahedron Letters, 26, 3915-3918 (1985).
Maryanoff et al., Carbohydrate Res., 171, 259-278 (1987).
Hanson et al., Inhibition of Gluconeogenesis and Glycogenolysis by 2,5-Anhydro-D-Mannitol, vol. 259, No. 1, Jan. 10, pp. 218-223, 1984.

Primary Examiner—Ronald W. Griffin
Attorney, Agent, or Firm—Alan M. Gordon

[57] ABSTRACT

Alpha-substituted phosphonates are disclosed which stimulate the enzyme fructose-1,6-bisphosphatase and inhibit the enzyme 6-phosphofructo-1-kinase, thereby lowering glucose levels in mammals. These alpha-substituted phosphonates may thus be used to treat hyperglycemia and/or diabetes. Processes for the synthesis of the alpha-substituted phosphonates are also disclosed.

29 Claims, No Drawings

ANTIDIABETIC ALPHA-SUBSTITUTED PHOSPHONATES

BACKGROUND OF THE INVENTION

This invention relates to novel organic compounds which are useful as pharmaceutical agents. The novel compounds of this invention modulate the activity of enzymes which control the processes of glycolysis and gluconeogenesis, two processes which help to regulate blood glucose levels in mammals. As such, the compounds of the present invention are useful for treating hyperglycemia and/or diabetes in warm-blooded animals. This invention also relates to methods for treating hyperglycemia and/or diabetes in mammals in need of such treatment, to pharmaceutical compositions for the utilization of these novel compounds in the treatment of hyperglycemia and/or diabetes and to processes for the chemical syntheses of these compounds.

The disease diabetes mellitus, commonly referred to as diabetes, is characterized by metabolic defects in the production and disposal of glucose. The result of these defects is the inability to maintain appropriate blood glucose (or blood sugar) levels. Treatments of diabetes have commonly employed the administration of exogenous insulin, the oral administration of drugs, or the use of dietary therapy. Initially, it was believed that the hyperglycemia observed in diabetics was simply the result of a deficiency in the supply of insulin, the principal hormone which controls glucose metabolism. As a result, research focused on the source of insulin production, the beta cells of the pancreas, and pharmaceutical agents which stimulated these cells to release insulin were developed.

Although it is true that a deficiency in insulin production can produce hyperglycemia, it has now been recognized that a variety of defects in metabolic processes can play a major role in the control of blood glucose levels. Metabolic processes which are important in this regard include glycolysis (the metabolic degradation of glucose to lactic acid), gluconeogenesis (the metabolic process by which endogenous synthesis of glucose from lactic acid occurs), glycogenolysis (the metabolic process by which glucose is released from stored glycogen), and insulin-stimulated glucose uptake (the metabolic process by which peripheral tissues acquire glucose as an energy source). Defects in any or all of these metabolic processes have significant effects on the maintenance of appropriate blood glucose levels.

In Type I diabetes, also called juvenile-onset or insulin-dependent diabetes, a deficiency in insulin production is the major cause of hyperglycemia. However, the majority of diabetics suffer from a form of the disease referred to as Type II, also called maturity-onset or noninsulin-dependent diabetes. In most Type II diabetics, basal insulin levels are normal or even elevated; in spite of this, transient or continuous elevations in blood glucose levels occur. In such disease states, the metabolic processes mentioned above, which normally function to provide exquisite control over blood glucose levels, are operating in an aberrant manner. Thus, a pharmaceutical agent capable of regulating these processes would be useful in restoring normal metabolic control of blood sugar levels.

Two of the above-described metabolic processes which are vitally important to glucose homeostasis are glycolysis and gluconeogenesis. In the process called glycolysis, glucose is converted in a series of enzymatically catalyzed transformations to lactic acid. In the process called gluconeogenesis, glucose is synthesized from lactic acid in another series of enzymatically catalyzed transformations. It is well known that proper regulation of these two metabolic processes is essential for the maintenance of appropriate blood glucose levels.

In recent years, research has resulted in the discovery of a natural product, beta-D-fructose-2,6-bisphosphate (Pilkis et al., *J. Biol. Chem* 256, 3171–3174 (1981)), which has now been demonstrated to be an important regulator of both glycolysis and gluconeogenesis Beta-D-fructose-2,6-bisphosphate exerts its regulatory action on these metabolic processes by specifically modulating the activity of a key enzyme involved in each of these processes. First, beta-D-fructose-2,6-bisphosphate promotes glycolysis by stimulating the enzyme 6-phosphofructo-1-kinase, which catalyzes the conversion of fructose-6-phosphate to fructose-1,6-bisphosphate. Second, beta-D-fructose-2,6-bisphosphate attenuates gluconeogenesis by inhibiting the enzyme fructose-1,6-bisphosphatase, which catalyzes the conversion of fructose-1,6-bisphosphate to fructose-6-phosphate. Either or both of these regulatory actions serve to reduce glucose levels, the former by promoting the metabolic degradation of glucose and the latter by attenuating the endogenous synthesis of glucose. Thus, the net result of the regulatory action of beta-D-fructose-2,6-bisphosphate is a lowering of glucose levels, the exact result desired in the treatment of hyperglycemic and/or diabetic states.

It has now been found that the novel organic compounds of the present invention exert regulatory actions on the key enzymes of the glycolytic and gluconeogenic processes in exactly the same manner as the natural product, beta-D-fructose-2,6-bisphosphate. The novel compounds are more resistant to enzymatic or hydrolytic degradation than the natural product, which has a labile acetal phosphate group. The novel compounds are stimulators of the enzyme 6-phosphofructo-1-kinase and inhibitors of the enzyme fructose-1,6-bis-phosphatase; the net result of these actions being the lowering of glucose levels. As such, they are useful for the treatment of hyperglycemic and/or diabetic states in mammals.

SUMMARY OF THE INVENTION

This invention relates to novel organic compounds of Formula I:

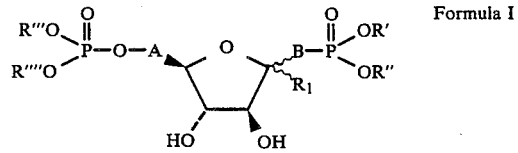

Formula I wherein A is selected from the group consisting of $C_1$ to $C_4$ alkylene and $C_2$ to $C_4$ hydroxyalkylene; B is selected from the group consisting of $C_1$ to $C_4$ alkylene and $C_2$ to $C_4$ hydroxyalkylene in which the carbon atom of the alkylene moiety which is adjacent to the phosphorous atom is mono- or disubstituted with a substituent selected from the group consisting of halogen, hydroxy and $C_1$ to $C_4$ alkoxy; $R_1$ is selected from the group consisting of hydrogen, $C_1$ to $C_4$ alkyl, $C_1$ to $C_4$ hydroxyalkyl, $C_2$ to $C_4$ dihydroxyalkyl, $C_3$ or $C_4$ trihydroxyalkyl and $C_4$ tetrahydroxyalkyl; $R'$, $R''$, $R'''$ and $R''''$ are selected independently from the group consisting of hydrogen, $C_1$ to $C_{18}$ alkyl, $C_3$ to $C_6$ cycloalkyl, phenyl, $C_3$ to $C_8$ isoalkyl, $Cl_3CCH_2-$, $CH_2=CHCH_2-$, $ZCH_2CH_2-$ [where Z is $SO_2R_2$, $SR_2$, $OR_2$ or $Si(R_2)_3$, and $R_2$ is $C_1$ to $C_3$ alkyl],

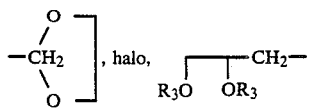

[where $R_3$ is $C_1$ to $C_3$ alkyl and $R_3-R_3$ is alkylene or acetal],

where $R_4$ is hydrogen or methyl),

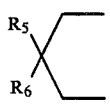

[where when $R_5=R_6$ they are both hydrogen, fluoro or $C_1$ to $C_4$ alkyl, $R_5$ is hydrogen, $R_6$ is fluoro, hydroxy or $OR_7$ [where $R_7$ is $C_1$ to $C_6$ alkyl, $C_3$ to $C_6$ cycloalkyl or aryl]]

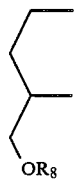

where $R_8$ is hydrogen or $C_1$ to $C_{18}$ alkyl],

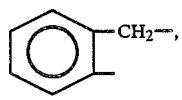

phenylmethyl, substituted phenylmethyl wherein the substituents are selected from $C_1$ to $C_{18}$ alkyl, $C_1$ to $C_6$ alkoxy, $NO_2$ and halogen, and mono- and disubstituted phenyl wherein the substituents are selected from $C_1$ to $C_{18}$ alkyl, $C_1$ to $C_6$ alkoxy, $NO_2$ and halogen; and, when any one or more of R', R", R''' or R'''' are hydrogen, the pharmacologically acceptable salts thereof.

This invention is also concerned with novel organic compounds of Formula II:

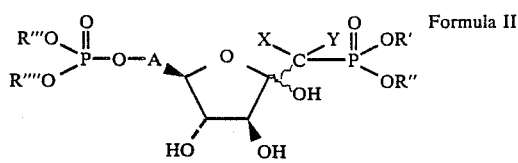

Formula II wherein A, R', R", R''' and R'''' are as described for Formula I; X and Y are selected independently from the group consisting of hydrogen, halogen, hydroxy and $C_1$ to $C_4$ alkoxy and, when any one or more of R', R", R''' or R'''' are hydrogen, the pharmacologically acceptable salts thereof.

This invention is further concerned with methods of treating hyperglycemia and/or diabetes in mammals in need of such treatment and to pharmaceutical compositions of matter employing compounds of the above Formula I and the above Formula II.

DETAILED DESCRIPTION OF THE INVENTION

Compounds of the present invention may be prepared according to the following flowcharts. In these flowcharts, the phenyl group

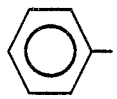

is abbreviated Ph.

Flowchart A

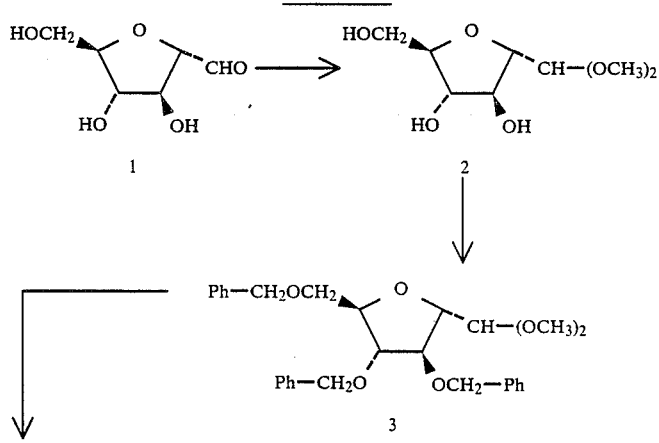

-continued
Flowchart A
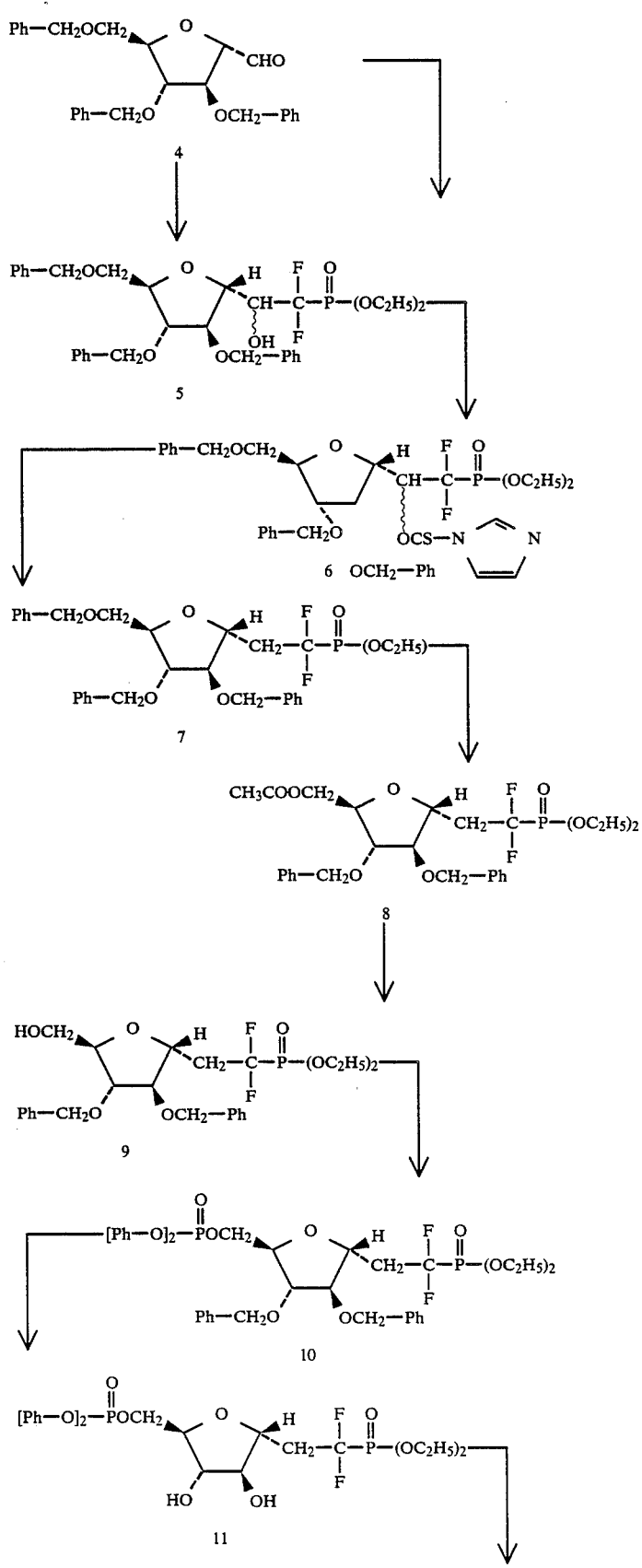

Flowchart A

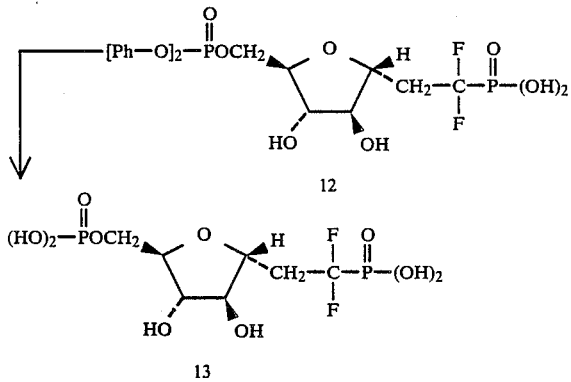

In accordance with Flowchart A, 2,5-anhydro-D-mannose 1 is treated with acetyl chloride in anhydrous methanol at reflux, followed by neutralization with lead carbonate, giving 2,5-anhydro-D-mannose, dimethyl acetal 2, which is treated with sodium hydride in dimethylformamide, followed by reaction with benzyl bromide, giving 2,5-anhydro-3,4,6-tris-O-(phenylmethyl)-D-mannose, dimethyl acetal 3, which is treated with tetrafluoroboric acid in acetonitrile, giving 2,5-anhydro-3,4,6-tris-O-(phenylmethyl)-D-mannose 4. Compound 4 is reacted with a solution of lithiodiisopropylamine in tetrahydrofuran, and (difluoromethyl) phosphonic acid, diethyl ester at −75° C., giving a mixture of 3,6-anhydro-1-deoxy-(diethoxyphosphinyl)-1,1-difluoro-4,5,7-tris-O-(phenylmehyl)-D-olvcero-D-galacto-heptitol and 2,5-anhydro-7-deoxy-7-(diethoxyphsophinyl)-7,7-difluoro-1,3,4-tris-O-(phenylmethyl)-D-glycero-Dmanno-heptitol, 5. The mixture 5 is reacted with N,N'-thiocarbonyldiimidazole in tetrahydrofuran, giving a mixture of 3,6-anhydro-1-deoxy-1-(diethoxyphinyl)-1,1-difluoro-4,5,7-tris-O-(phenylmethyl)-D-glycero-D-galacto-heptitol, 0-1H-imidazole-1-carbothioate and 2,5-anhydro-7-deoxy-7-(diethoxyphosphinyl)-7,7-difluoro-1,3,4-tris-O-(phenylmethyl)-D-glycero-D-manno-heptitol, 0-1H-imidazole-1-carbothioate 6. The mixture 6 is treated with n-tributyl stannous hydride and 2,2'-azobisisobutyronitrile in dry toluene under argon with heat, then purified by chromatography, giving 3,6-anhydro-1,2-dideoxy-1-(diethoxyphosphinyl)-1,1-difluoro-4,5,7-tris-O-(phenylmethyl)-D-manno-heptitol 7, which is treated first with boron trifluoride etherate in acetic anhydride at 0° C., giving acetate derivative 8, which is reacted with sodium ethoxide in ethanol under argon, giving 3,6-anhydro-1,2-dideoxy-1-(diethoxyphosphinyl)-1,1-difluoro-4,5-bis-O-(phenylmethyl)-D-manno-heptitol 9. Compound 9 is treated with diphenyl chlorophosphate in pyridine under argon at ice bath temperature, giving 3,6-anhydro-1,2-dideoxy-1-(diethoxyphosphinyl)-1,1-difluoro-3,4-bis-O-(phenylmethyl)-D-manno-heptitol, 7-(diphenyl phosphate) 10 which is catalytically hydrogenated, giving 3,6-anhydro-1,2-dideoxy-1-(diethoxyphosphinyl)-1,1-difluoro-D-manno-heptitol, 7-(diphenyl phosphate) 11. Compound 11 is treated with trimethylsilyl bromide in deuterated chloroform under argon, giving 3,6-anhydro-1,2-dideoxy-1,1-difluoro-1-phosphono-D-manno-heptitol, 7-(diphenyl phosphate) 12 which is then catalytically hydrogenated giving the product 3,6-anhydro-1,2-dideoxy-1,1-difluoro-1-phosphono-D-manno-heptitol, 7-dihydrogen phosphate 13.

Flowchart B

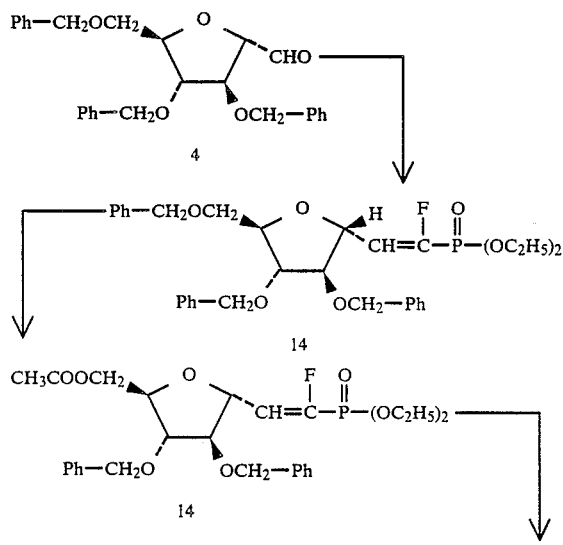

-continued

Flowchart B

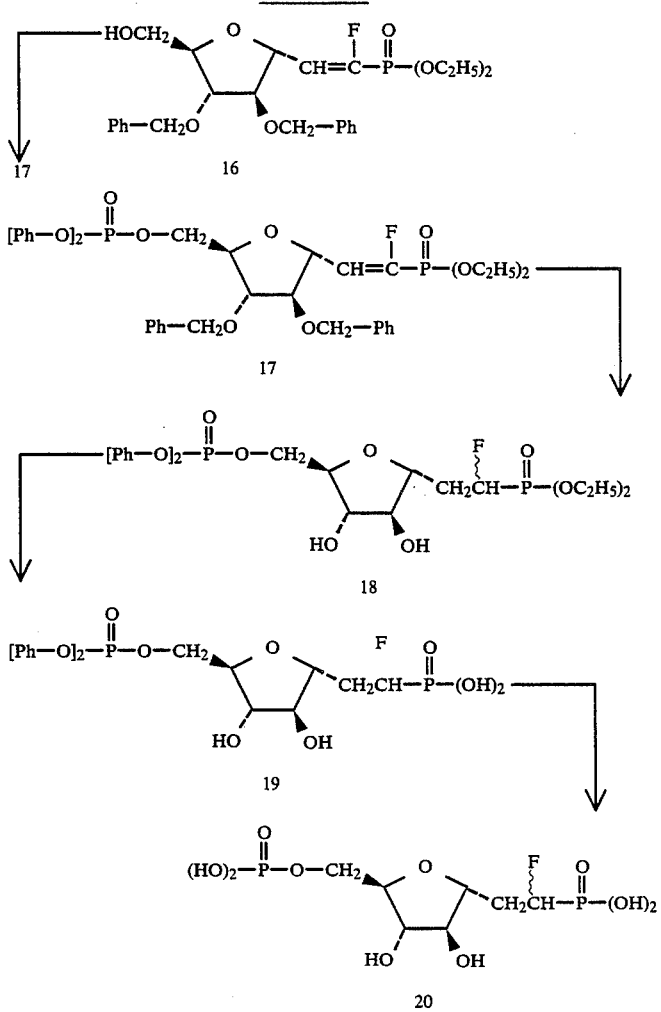

In accordance with Flowchart B, 2,5-anhydro-3,4,6-tris-O-(phenylmethyl)-D-mannose 4, is treated with a reagent prepared by treating tetraethyl difluoromethylene diphosphonate with n-butyl lithium in ether, giving (E)-3,6-anhydro-1,2-dideoxy-1-(diethoxyphsophinyl)-1-fluoro-4,5,7-tris-O-(phenylmethyl)-D-manno-1-hept-1-enitol 14, which is reacted first with acetic anhydride and boron trifluoride etherate to give the acetate derivative 15 and then with sodium ethoxide in ethanol, giving (E)-3,6-anhydro-1,2-dideoxy-1-(diethoxyphosphinyl)-1--fluoro-4,5-bis-O-(phenylmethyl)---D-manno-hept-1-enitol 16. Compound 16 is then treated with diphenyl chlorophosphate in pyridine, giving (E)-3,6-anhydro-1,2-dideoxy-1-(diethoxyphosphinyl)-1-fluoro-4,5-bis-O-(phenylmethyl)-D-manno-hept-1-enitol, 7-(diphenyl phosphate) 17, which is then hydrogenated over palladium on carbon, giving a mixture of [1R(and 1S)]-3,6-anhydro-1,2-dideoxy-1-(diethoxyphosphinyl)-1-fluoro-D-manno-heptitol, 7-(diphenyl phosphate) 18. Compound 18 is then treated with trimethylsilyl bromide in deuterated chloroform giving [1R(and 1S)]-3,6-anhydro-1,2-dideoxy-1-fluoro-1-phosphono-D-manno-heptitol, 7-(diphenyl phosphate) 19 as a mixture, which is hydrogenated over platinum oxide in methanol, giving as a mixture [1R(and 1IS)]-3,6-anhydro-1,2-dideoxy-1-fluoro-1-phosphono-D-manno-heptitol, 7-(dihydrogen phosphate) 20.

Flowchart C

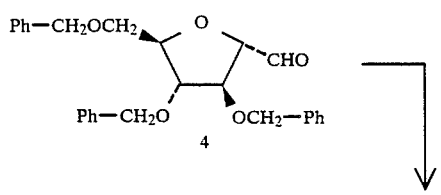

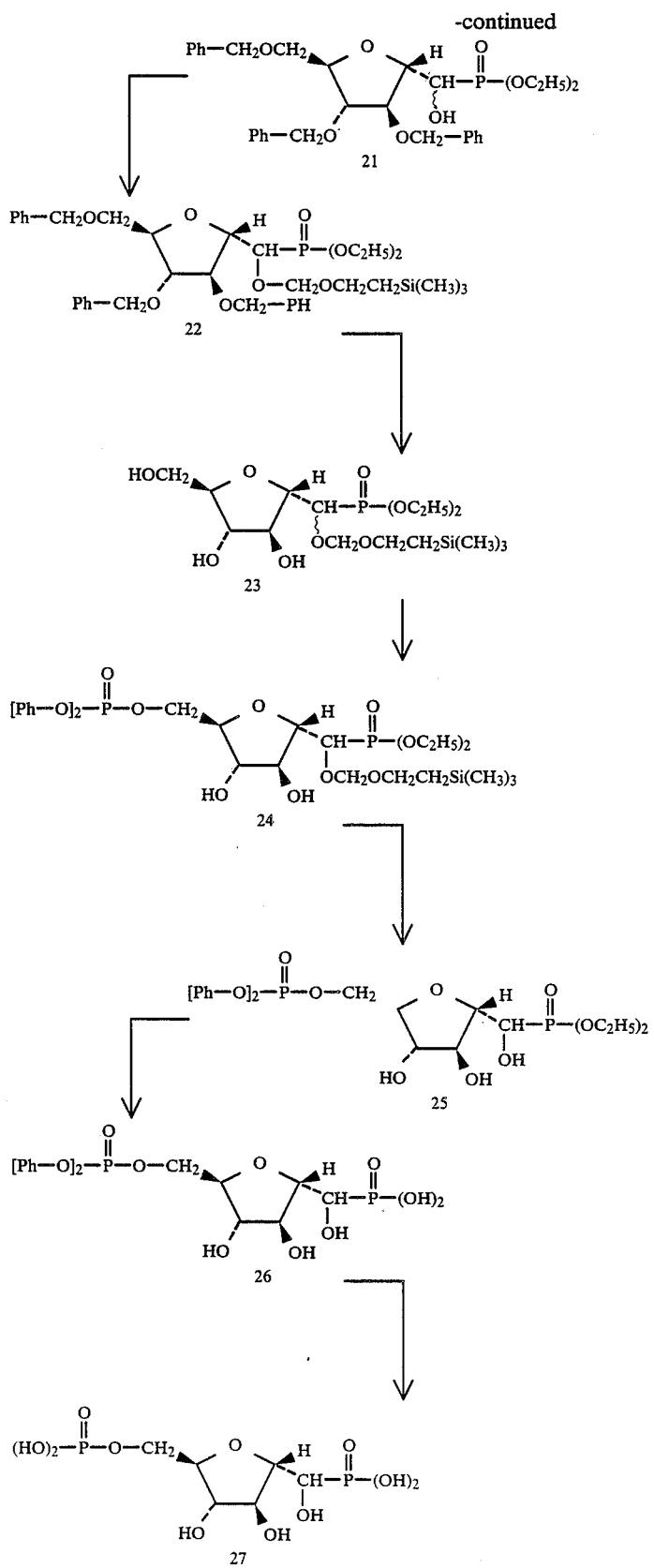
In accordance with Flowchart C, 2,5-anhydro-3,4,6-tris-O-(phenylmethyl)-D-mannose 4 is reacted with diethyl phosphite and sodium ethoxide under argon, giving [1R(and/or 1S)]-2,5-anhydro-1-C-(diethoxyphosphinyl)-3,4,6-tris-O-(phenylmethyl)-D-glucitol 21, which is reacted with N,N-diisopropylethylamine and 2-(trimethylsilyl)ethoxymethyl chloride in dry dichloromethane under argon at reflux, giving [1R-(and/or 1S)]-2,5-anhydro-1-C-(diethoxyphosphinyl)-3,4,6-tris-O-(phenylmethyl)-1-O-[[2-(trimethylsilyl)ethoxy]methyl]-D-mannitol 22. Compound 22 is hydrogenated in methanol over palladium hydroxide on carbon, giving [1R(and/or 1S)]-2,5-anhydro-1-C-(diethoxyphosphi8-nyl)-1-O-[[2-(trimethylsilyl)ethoxy]methyl]-D-mannitol 23 which is then reacted with diphenyl chlorophosphate in pyridine at ice bath temperature, giving [1R(and/or 1S)]-2,5-anhydro-1-C-(diethoxyphosphinyl)-1-0-[[2-(trimethylsilyl)ethoxy]methyl]-D-mannitol, 6-(diphenyl phosphate) 24. Compound 24 is reacted with boron trifluoride etherate in anhydrous acetonitrile under argon, giving [1R(and/or 1S)]-2,5-anhydro-1-C-(diethoxyphosphinyl)-D-mannitol, 6-(diphenyl phosphate) 25 which is then reacted with bromotrimethylsilane in deuterated chloroform under argon, giving [1R(and/or 1S)]-2,5-anhydro-1-C-phosphono-D-mannitol, 6-(diphenyl phosphate) 26 which is hydrogenated in methanol over platinum oxide, giving [1R(and/or 1S)]-2,5-anhydro-1-C-phosphono-D-mannitol, 6-(dihydrogen phosphate) 27.

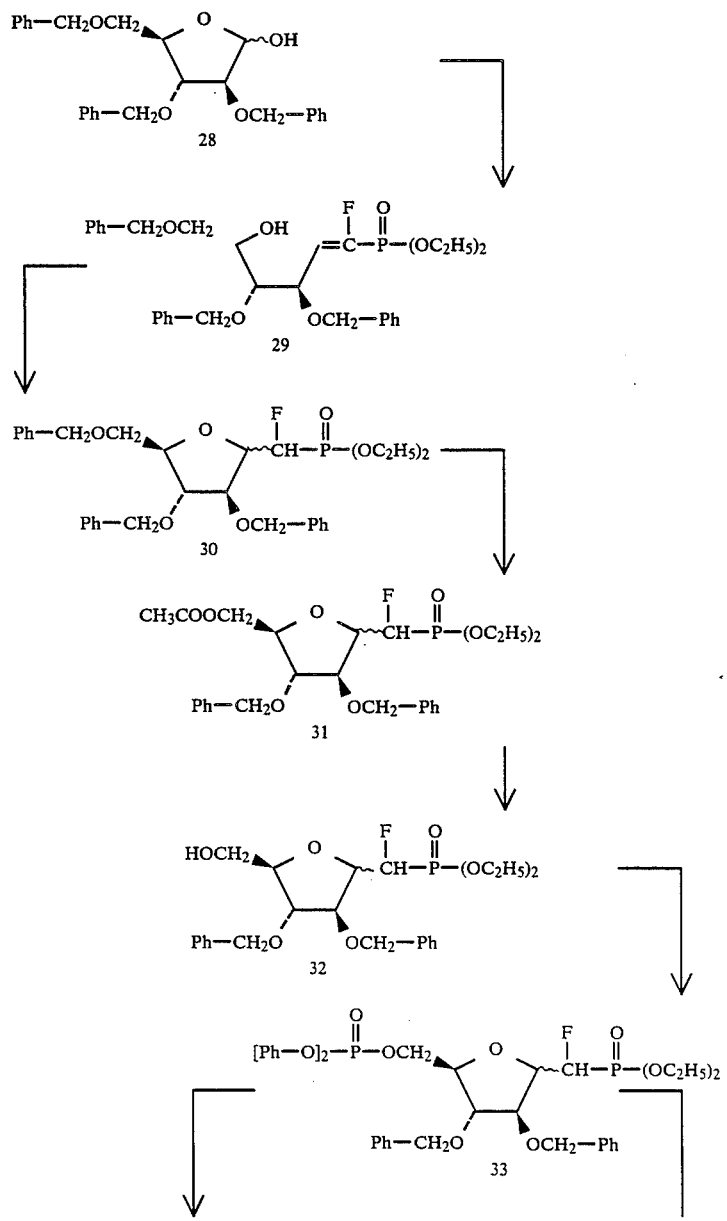

Flowchart D

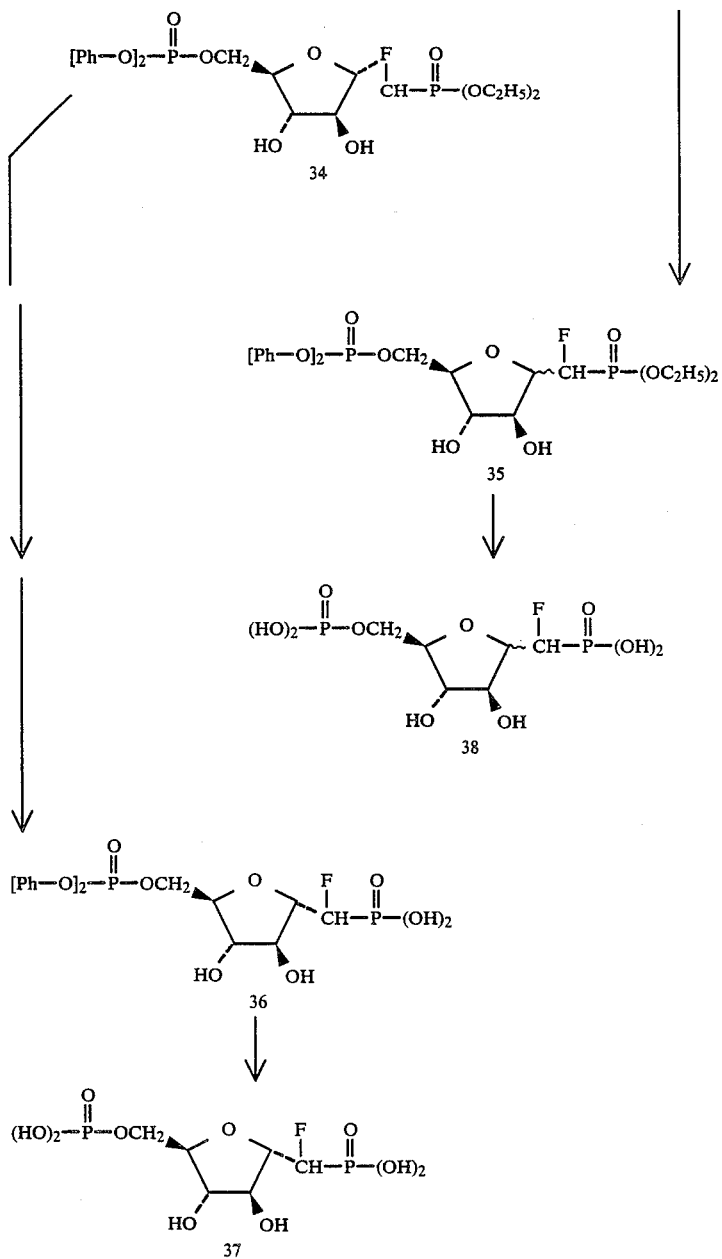

In accordance with Flowchart D, 2,3,5-tris-O-(phenylmethyl)-D-arabinofuranose 28 is reacted with lithiodiisopropylamine and (fluoromethyl) diphosphonic acid, diethyl ester in tetrahydrofuran at −75° C., giving 1,2-dideoxy-1-(diethoxyphosphinyl)-1-fluoro-3,4,6-tris-O-(phenylmethyl)-D-arabino-hex-1-enitol 29, which is treated with sodium ethoxide in ethanol under argon followed by acidification, giving 2,5-anhydro-1-deoxy-1-(diethoxyphosphinyl)-1-fluoro-3,4,6-tris-O-(phenylmethyl)-D-glucitol and D-mannitol mixture 30. Compound 30 in acetic anhydride at ice bath temperature is treated with boron trifluoride etherate, then with saturated sodium bicarbonate, giving acetate derivative 31 which is treated with sodium ethoxide in ethanol under argon, giving 2,5-anhydro-1-deoxy-1-(diethoxyphosphinyl)-1-fluoro-3,4-bis-O-(phenylmethyl)-D-glucitol and D-mannitol mixture 32. Compound 32 in pyridine at 0° C. under argon is treated with diphenylchlorophosphate, giving 2,5-anhydro-1-deoxy-1-(diethoxyphosphinyl)-1-fluoro-3,4-bis-O-(phenylmethyl)-D-glucitol and D-mannitol, diphenyl phosphate mixture 33. The mixture 33 is hydrogenated in methanol over palladium hydroxide and then separated by flash chromatography, giving 2,5-anhydro-1-deoxy-1-C-(diethoxyphosphinyl)-1-fluoro-D-mannitol, 6-(diphenyl phosphate) 34, and a mixture of D-mannitol and D-glucitol derivatives, 35. Compound 34 in deuterated chloroform is treated with trimethylsilyl bromide under argon, giving 2,5-anhydro-1-deoxy-1-fluoro-1-phospho-D-mannitol, 6-(diphenyl phosphate) 36 which is hydrogenated in methanol over platinum oxide, giving 2,5-anhydro-1-deoxy-1-fluoro-1-phosphono-D-mannitol, 6-(dihydrogen phosphate) 37. The mixture 35 is hydrogenated in the same manner, giving 2,5-anhydro- 1-deoxy-1-fluoro-1-phosphono-D-glucitol and D-mannitol, 6-(dihydrogen phosphate) as a 70:30 mixture 38.
Flowchart E
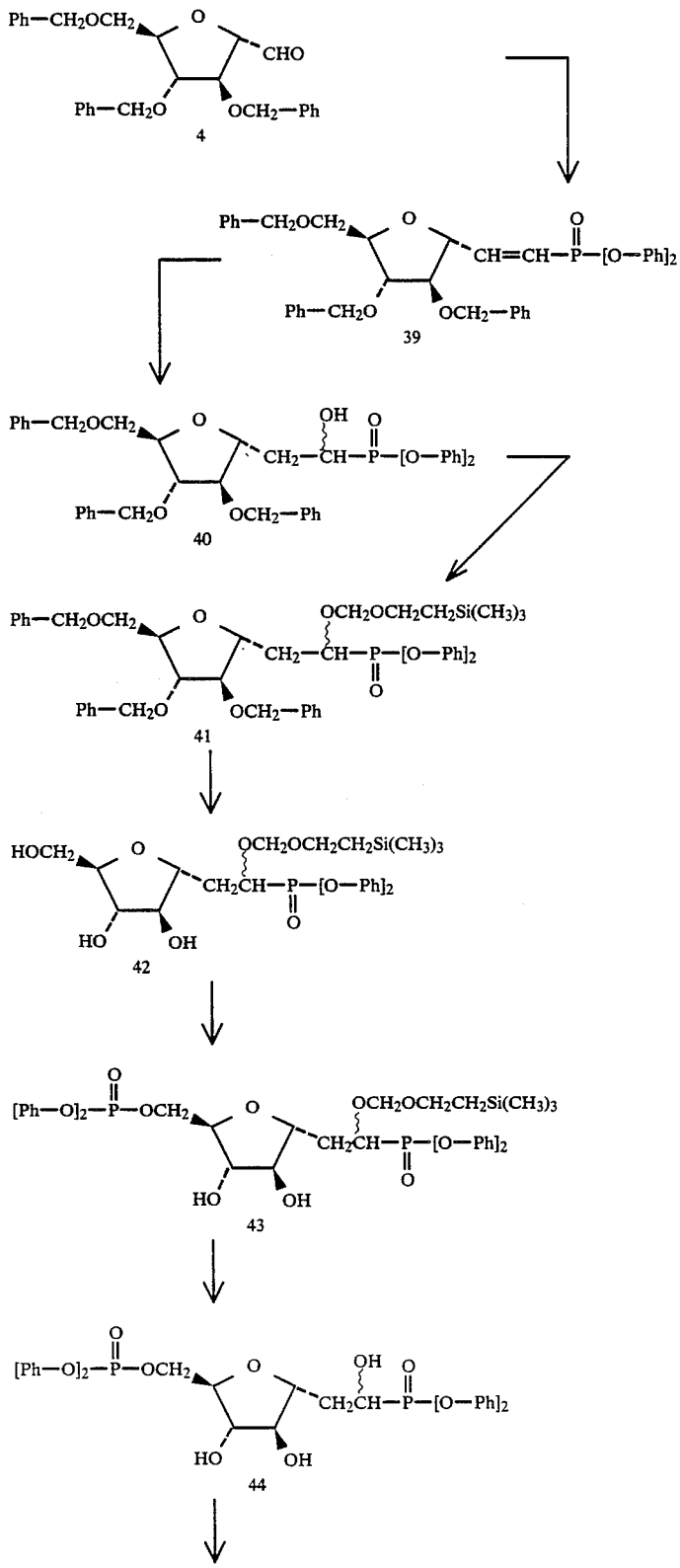

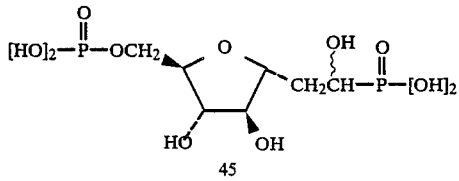

45

In accordance with Flowchart E, 2,5-anhydro-3,4,6-tris-O-(phenylmethyl)-D-mannose 4 is reacted with triphenylphosphoranylidinemethylphosphonate in anhydrous toluene at reflux, giving (E)-3,6-anhydro-1,2-dideoxy-1-(diphenoxyphosphinyl)-4,5,7-tris-O-(phenylmethyl)-D-manno-heptitol 39. which is reacted with borane-tetrahydrofuran complex in anhydrous tetrahydrofuran at ice/salt bath temperature, then treated with cold aqueous sodium hydroxide and 30% hydrogen peroxide, giving a mixture of 3,6-anhydro-2-deoxy-1-C-(diphenoxyphosphinyl)-4,5,7-tris-O-(phenylmethyl)-D-glycero-D-galacto-heptitol and 2,5-anhydro-6-deoxy-7-C-(diphenoxyphosphinyl)-1,3,4-tris-O-(phenylmetyl)-D-glycero-D-manno-heptitol 40. Compound 40 is then reacted with diisopropylethylamine, followed by 2-(trimethylsilyl)ethoxymethyl chloride in dichloromethane under an inert atmosphere, giving [1R(and 1S)]-3,6-anhydro-2-deoxy-1-C-(diphenoxyphosphinyl)-4,5,7-tris-O-(phenylmethyl)-1-O-[[2-(trimethylsilyl)ethoxy]-methyl]-D-manno-heptitol 41, which is hydrogenated in methanol over palladium hydroxide giving [1R(and 1S)]-3,6-anhydro-2-deoxy-1-C-(diphenoxyphosphinyl)--1-O-[[2-(trimethylsilyl)ethoxy]methyl]-D---manno-heptitol 42. Compound 42 is treated with diphenyl chlorophosphate in pyridine at 0° C., giving [1R(and 1S)]-3,6-anhydro-2-deoxy-1-C-(diphenoxyphosphinyl)-1-O-[[2-(trimethylsilyl)ethoxy]-methyl]-D-manno-heptitol, 7-(diphenyl phosphate) 43. Using other substituted chlorophosphates in the reaction from 42 to 43 will produce the corresponding esters analogous to 43. Compound 43 is then reacted with boron trifluoride etherate in acetonitrile under an inert atmosphere, giving the product [1R(and/or 1S)]-3,6-anhydro-2-deoxy-1-C-(diphenoxyphosphinyl)-D-manno-heptitol, 7-(diphenyl phosphate) 44. Product 44 is hydrogenated in methanol over platinum oxide to produce the product [1R(and/or 1S)]-3,6-anhydro-2-deoxy-1-phosphono-D-manno-heptitol, 7-(dihydrogen phosphate) 45.

Flowchart F

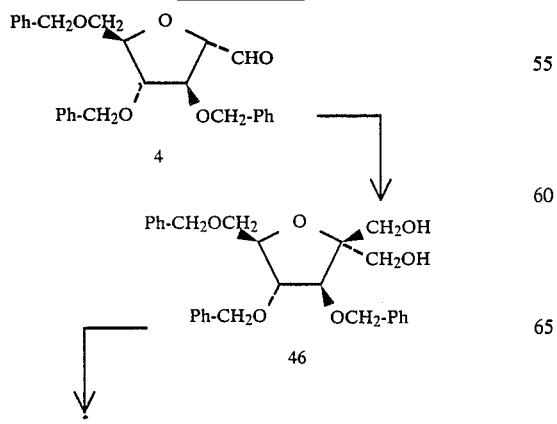

-continued
Flowchart F

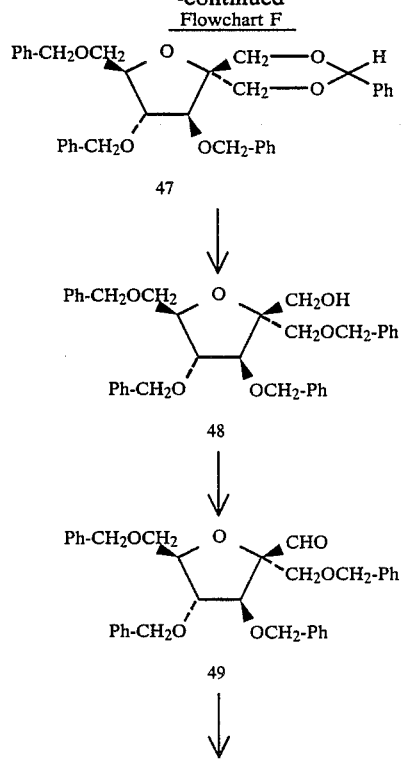

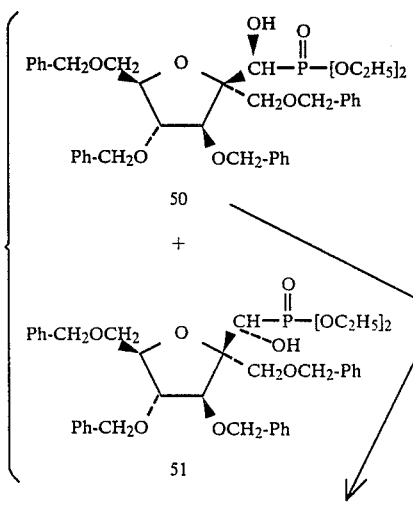

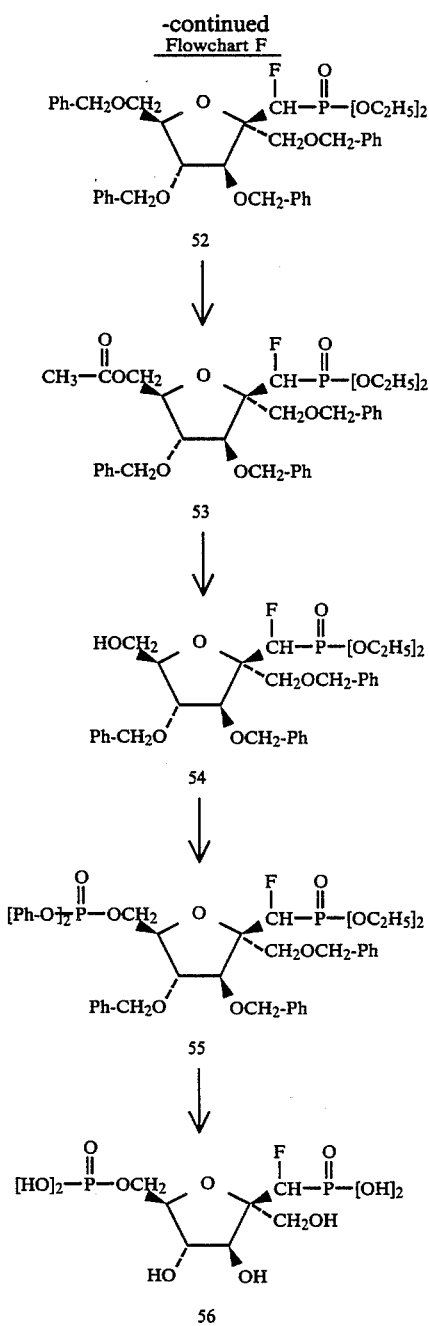

water, giving 2,5-anhydro-2-C-[(phenylmethoxy)methyl]-3,4,6-tris-O--(phenylmethyl)-D-glucose 49. Compound 49 is dissolved in diethyl phosphite, treated with triethylamine under argon, then with acetic acid, giving [1R(and 1S)]-2,5-anhydro-1-C-(diethoxyphosphinyl)-2-C-[(phenylmethoxy) methyl]-3,4,6-tris-O-(phenylmethyl)-D-glucitol 50 and 51, which are separated by chromatography. The major, less polar isomer of 50 and 51 (not identified) is treated with diethylamino sulfur trifluoride in dry dichloromethane, followed by saturated sodium bicarbonate, giving [1R(or 1S)]-2,5-anhydro-1-deoxy-1-(diethoxyphosphinyl)-1-fluoro-2-C-[(phenylmethoxy)-methyl]-3,4,6-tris-O-(phenylmethyl)-D-glucitol 52. Compound 52 is treated with boron trifluoride etherate in acetic anhydride at 0° C. under argon, followed by sodium bicarbonate, giving 2,5-anhydro-1-deoxy-1-(diethoxyphosphinyl)-1-fluoro-2-C-[(phenylmethoxy)methyl]-3,4-bis-0-(phenylmethyl)-D-glucitol, acetate 53 which is treated with sodium ethoxide in ethanol under argon followed by acetic acid, giving 2,5-anhydro-1-deoxy-1-(diethoxyphosphinyl)-1-fluoro-2-C-[(phenylmethoxy) methyl]-3,4-bis-O-(phenylmethyl)-D-glucitol 54. Compound 54 is treated with diphenyl chlorophosphate in cold pyridine, giving [1R(or 1S)]-2,5-anhydro-1-deoxy-1-(diethoxyphosphinyl)-1-fluoro-2-C-[(phenylmethoxy)methyl]-3,4-bis-O-(phenylmethyl)-D-glucitol, diphenyl phosphate 55 which is treated with trimethylsilyl bromide in deuterated chloroform under argon, followed by sequential hydrogenation, first over palladium-on-carbon, then platinum oxide, both in methanol, to obtain the desired product 2,5-anhydro--1-deoxy-1-fluoro-2-(hydroxymethyl)-1-phosphono-D-glucitol, 6-(dihydrogen phosphate) 56.

In accordance with Flowchart F, 2,5-anhydro--3,4,6-tris-O-(phenylmethyl)-D-mannose 4 is treated with 37% formalin and potassium carbonate in methanol at 85° C., then neutralized, giving 2,5-anhydro-2-C-(hydroxymethyl)-3,4,6-tris-O-(phenylmethyl)-D-arabinohexitol 46, which is reacted with benzaldehyde dimethyl acetal and p-toluenesulfonic acid in dimethylformamide at 60° C., giving 2,5-anhydro-2-C-(hydroxymethyl)-3,4,6--tris-O-(phenylmethyl)-1,2¹-O-(phenylmethylene)-[R(or S)]-glucitol 47. Compound 47 is reacted with lithium aluminum hydride and aluminum chloride in dichloromethane: ether (1:1) at 45°-50° C., then flash chromatographed to separate the desired glucitol compound 48, which is reacted with oxalyl chloride in dimethyl sulfoxide and dichloromethane under argon at −60° C. followed by treatment with triethylamine and Flowchart G

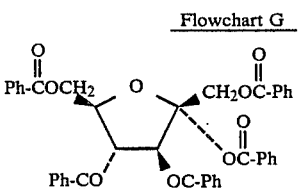

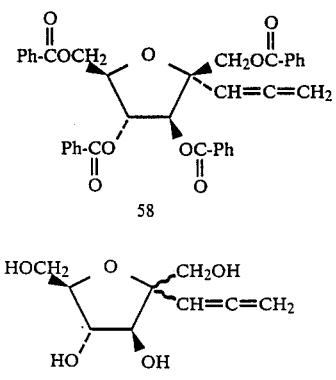

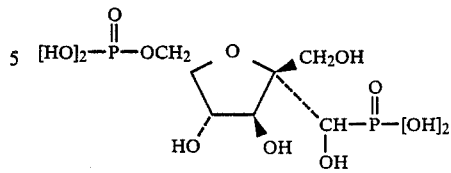
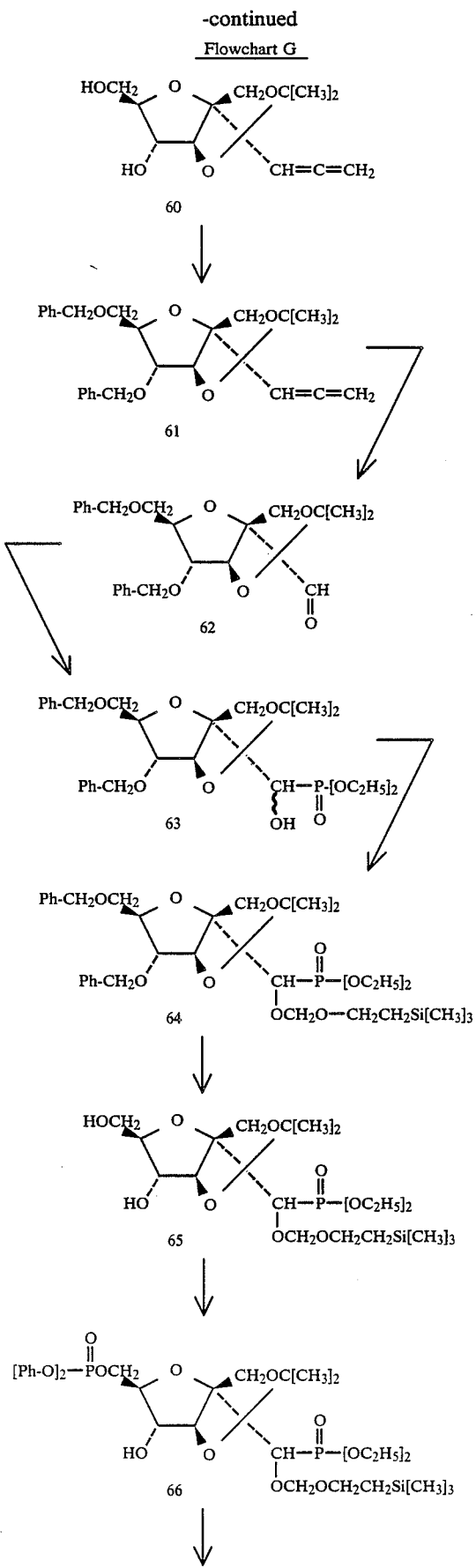

In accordance with Flowchart G, D-fructofuranose pentabenzoate 57 and propargyltrimethylsilane in acetonitrile at 0° C. are reacted with boron trifluoride etherate, giving 4,7-anhydro-4-C-[(benzoyloxy)methyl]-1,2,3-trideoxy-D-manno-octa-1,2-dienitol, tribenzoate 58, which is treated with sodium methoxide in methanol, giving 4,7-anhydro-1,2,3-trideoxy-4-C-(hydroxymethyl)-D-oluco (or D-manno)-octa-1,2-dienitol 59. Compound 59 is treated with cupric sulfate and sulfuric acid in acetone followed by sodium carbonate in pyridine, giving 4,7:4¹,5-dianhydro-1,2,3-trideoxy-4-C-[(1-hydroxy-1-methylethoxy)methyl]-D-manno-octa-1,2-dienitol 60 which is reacted with sodium hydride in dimethylformamide at 0° C. and then with 15 benzyl bromide and methanol, giving 4,7:4¹,5-dianhydro-1,2,3-trideoxy-4-C-[(1-hydroxy-1-methylethoxy)methyl]-6,8-bis-O-(phenylmethyl)-D-manno-octa-1,2-dienitol 61. Compound 61 is ozonized at −78° C. in dichloromethane containing pyridine, then treated with zinc dust and acetic acid, giving 2,5:2¹,3-dianhydro--2-C-[(1-hydroxy-1-methylethoxy)methyl]-4,6-bis-O-(phenylmethyl)-D-mannose 62, which is dissolved in diethyl phosphite and reacted with sodium ethoxide in ethanol, followed by sodium dihydrogen phosphate in dichloromethane, giving 2,5-anhydro-2-C-[(diethoxyphosphinyl)hydroxymethyl]-1,3-0-(1-m⒠thylethylidene)-4,6--bis-O-(phenylmethyl)-D-glucitol 63. Compound 63 is treated with diisopropylethylamine and 2-(trimethylsilyl)ethoxymethyl chloride in dichloromethane, giving 2,5-anhydro-2-C-[(diethoxyphosphinyl)[[2-(trimethylsilyl)ethoxy]methoxy]methyl]-1,3-O-(1-methylethylidene)-4,6-bis-O-(phenylmethyl)-D-glucitol 64, which is hydrogenated in methanol over palladium hydroxide on carbon, giving 2,5-anhydro-2-C-[(diethoxyphosphinyl)-[[2-(trimethylsilyl)ethoxy]methoxy]methyl]-1,3-O-(1-methylethylidene)-D-glucitol 65. Compound 65 is reacted with diphenyl phosphorochloridate in pyridine at 0° C., giving 2,5-anhydro-2-C-[(diethoxyphosphinyl)-[[2-(trimethylsilyl)ethoxy]methoxy]methyl]-1,3-O-(1-methylethylidene)-D-glucitol, 6-(diphenyl phosphate) 66, which is reacted with bromotrimethylsilane in dichloromethane, then hydrogenated in ethanol over platinum oxide, giving 2,5-anhydro-2-C-(hydroxyphosphonomethyl)-D-glucitol, 6-(dihydrogen phosphate) 67.

Flowchart H

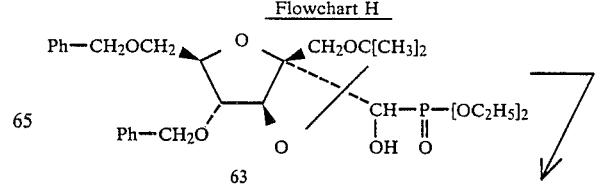

-continued
Flowchart H

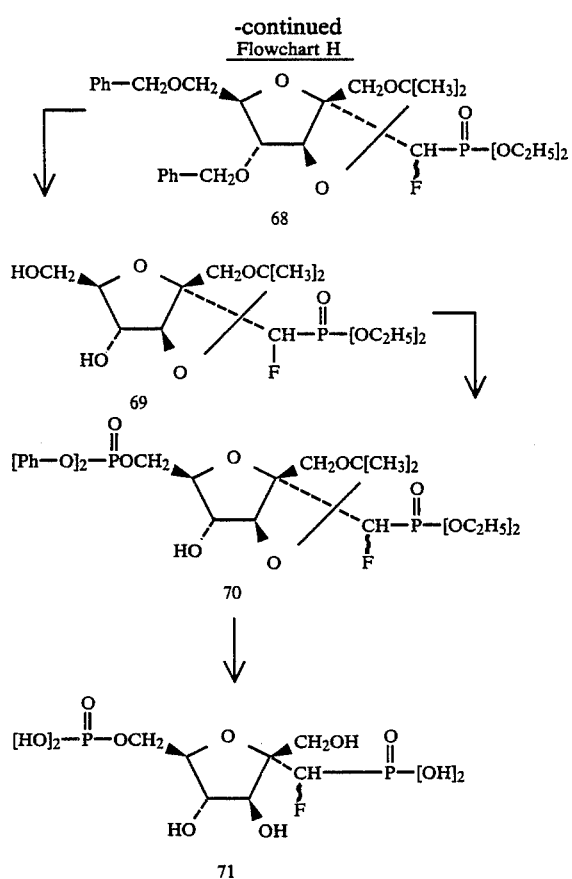

In accordance with Flowchart H, 2,5-anhydro--2-C-[(diethoxyphosphinyl)hydroxymethyl]-1,3-O-(1-methylethylidene)-4,6-bis-O-(phenylmethyl)-D-glucitol 63 is reacted with diethylaminosulfur trifluoride in dichloromethane at 0° C., then with sodium bicarbonate, giving 2,5-anhydro-2-C-[(diethoxyphosphinyl)fluoromethyl]-1,3-O-(1-methylethylidene)-4,6-bis-O-(phenyl- methyl)-D-glucitol 68, which is refluxed with Raney nickel in ethanol, then hydrogenated over palladium hydroxide, giving 2,5-anhydro-2-C-[(diethoxyphosphinyl)fluoromethyl]--1,3-O-(1-methylethylidene)--D-glucitol 69. Compound 69 is treated with diphenyl phosphorochloridate in pyridine at 0° C., giving 2,5-anhydro-2-C-[(diethoxyphosphinyl)fluoromethyl]1,3-O-(1-methylethylidene)-D-glucitol, 6-(diphenyl phosphate) 70, which is reacted with bromotrimethylsilane and then hydrogenated in ethanol over platinum oxide, giving 2,5-anhydro-2-C-(fluorophosphonomethyl)-D-glucitol, 6-(dihydrogen phosphate) 71.

Flowchart I

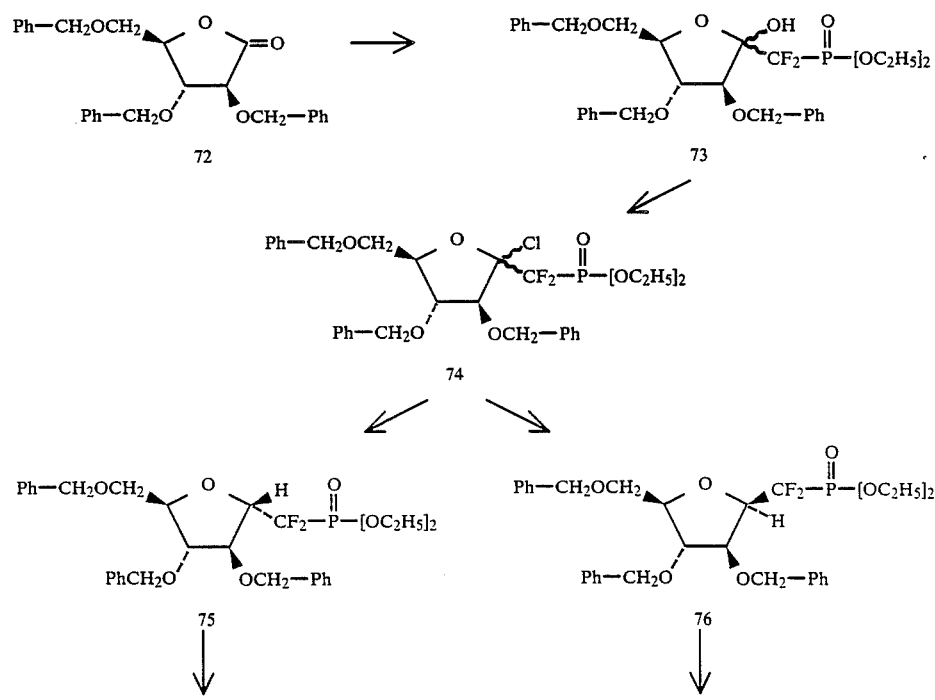

-continued
Flowchart I

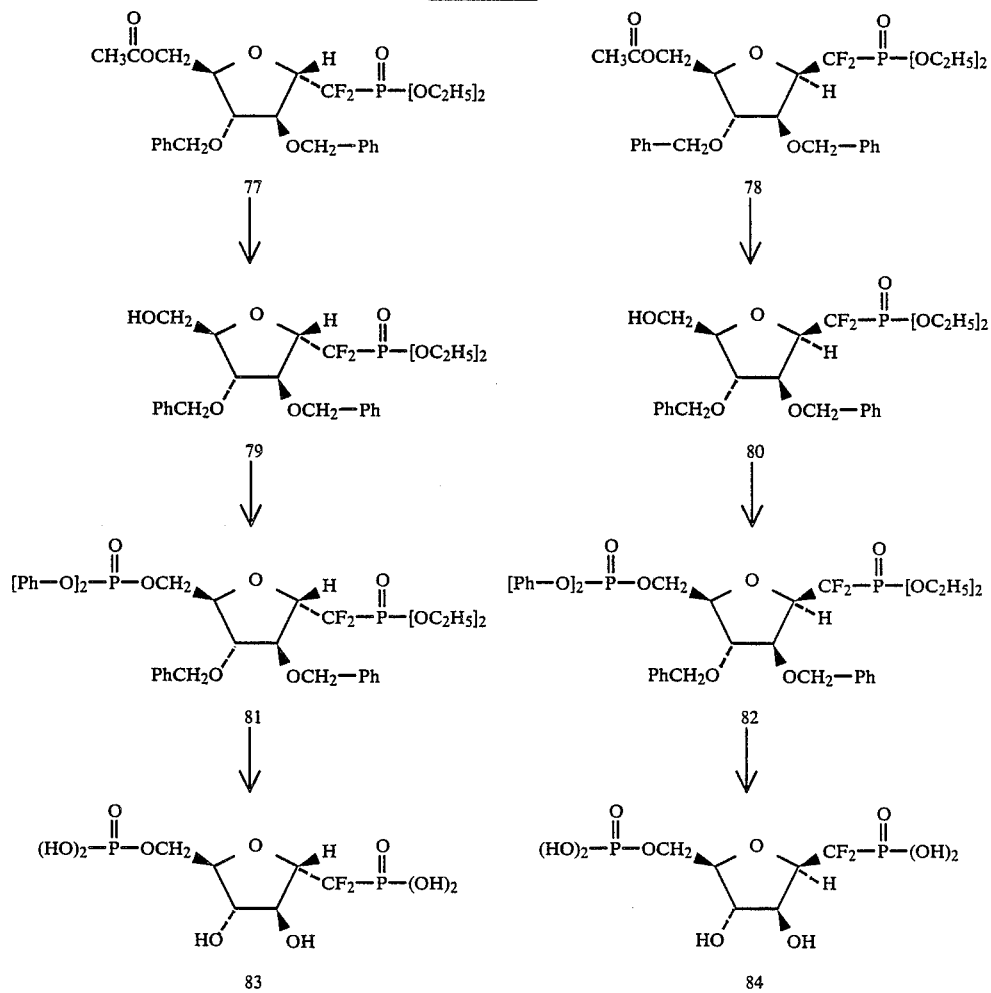

In accordance with Flowchart I, reaction of 2,3,5-tris-O-(phenylmethyl)-D-arabinonic acid, gammalactone 72 with (diethylphosphinyl)difluoromethyllithium provides the furanose 73. Treatment of 73 with a solution of thionyl chloride in dichloromethane in the presence of dimethylformamide provides the furanosyl chloride 74. Reduction of 74 with tributyltin hydride provides a separable mixture of 2,5-anhydro-1-(diethoxyphosphinyl)-D-mannitol derivative 75 and 2,5-anhydro-1-(diethoxyphosphinyl)-D-glucitol derivative 76. The derivatives 75 and 76 are treated separately but identically with boron trifluoride etherate in acetic anhydride giving the monoacetates 77 and 78 which are treated with ethanolic sodium ethoxide, providing the 6-hydroxy derivatives 79 and 80. Derivatives 79 and 80 are phosphorylated with diphenyl phosphorochloridate in pyridine providing derivatives 81 and 82 which are then diethylated with bromotrimethylsilane followed first by hydrogenolysis over palladium on carbon and then hydrogenolysis over platinum on carbon, giving the products 2,5-anhydro-1-deoxy-1,1-difluoro--1-phosphono-D-mannitol, 6-(dihydrogen phosphate) 83 and the corresponding D-glucitol derivative 84.

Flowchart J

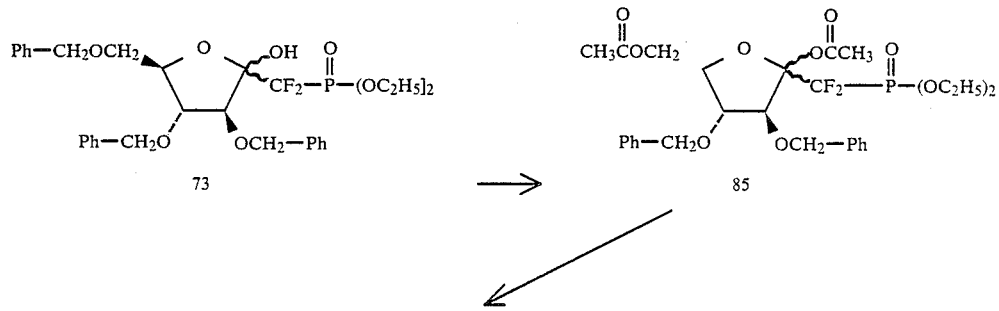

-continued
Flowchart J

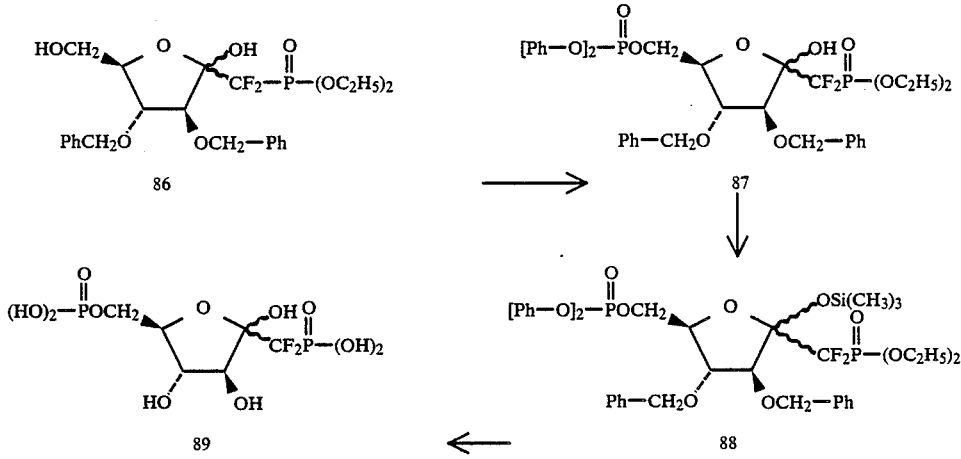

In accordance with Flowchart J, treatment of the furanose 73 with boron trifluoride etherate in acetic anhydride to effect selective debenzylation of the primary benzyl ether provides the diacetate 85, which is then deacetylated with ethanolic sodium ethoxide to provide the diol 86. Diol 86 is phosphorylated with diphenyl phosphorochloridate in pyridine providing the phosphate triester 87. The remaining hydroxyl group in 87 is protected by reaction with N,O-bis(trimethylsilyl)acetamide giving the furanose trimethylsilyl ether 88. Deprotection of 88 by successive reaction with bromotrimethylsilane in dichloromethane, hydrogenolysis in the presence of palladium on carbon and hydrogenation in the presence of platinum affords 1-deoxy-1,1-difluror-1-phosphono-D-fructfuranose, 6-dihydrogen phosphate, 89.

Certain of the phosphate esters of Formula I may be prepared by reacting an alcohol or aldehyde represented by structures I–IV in Table I with the reagents described in Tables IV–VIII to produce the bisphosphonates structurally represented by V–XI in Table I.

TABLE I

| Starting Material | Reagent | Procedure | Phosphonates |
|---|---|---|---|
| I | $HCF_2-P(=O)(OR')(OR'')$ | Ex. 4 | V |
| I | $[HCF-P(=O)(OR')(OR'')]_2$ | Ex. 11 | VI |
| I | $HP(=O)(OR')(OR'')$ | Ex. 17 | VII |
| II | $[HCF-P(=O)(OR')(OR'')]_2$ | Ex. 23 | VIII |

TABLE I-continued

| Starting Material | Reagent | Procedure | Phosphonates |
|---|---|---|---|
| I | (Ph)₃P=CHP(O)(OR')(OR'') | Ex. 30 | IX |
| I | [HCH(P(O)(OR')(OR''))]₂ | Ex. 11 | IX |
| III | HP(O)(OR')(OR'') | Ex. 41 | X |
| IV | HP(O)(OR')(OR'') | Ex. 52 | XI |

The compounds V–XI (Table I) may be converted to the corresponding intermediate alcohols represented by compounds XII–XIX in Table II, using the procedures shown in Flowcharts A–H.

TABLE II

| Phosphonates | Alcohols |
|---|---|
| V | XII |
| VI | XIII |
| VII | XIV |
| VIII | XV |
| IX | XVI |
| X | XVII |

TABLE II-continued

| Phosphonates | Alcohols |
|---|---|
| 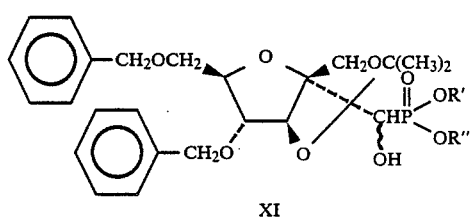 XI | 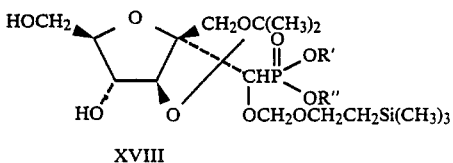 XVIII |
| 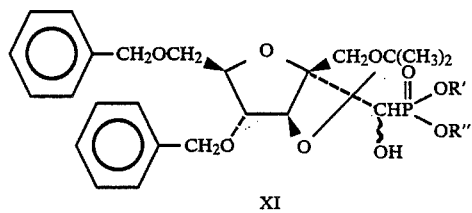 XI | 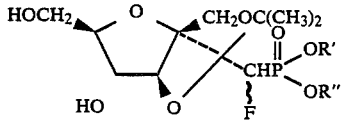 XIX |

The compounds XII–XIX may be phosphorylated using a suitable dialkyl, diaryl or alkyl aryl chlorophosphate reagent of the formula

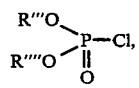

following the methods of Example 8 or 20 to provide the phosphate-phosphonate compounds XX–XXVII shown in Table III.

Examples of phosphorylating reagents which may be used in this reaction include those where R''' and R'''' are independently selected from straight or branched chain alkyl ($C_1$–$C_{18}$), phenylmethyl

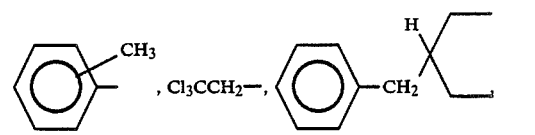

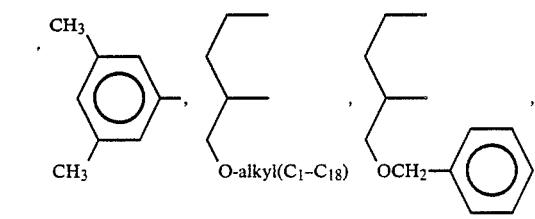

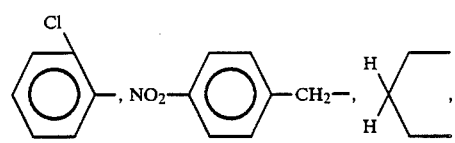

-continued

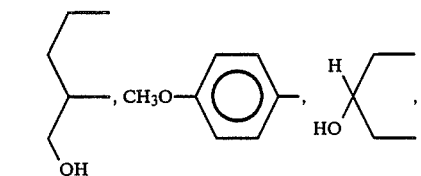

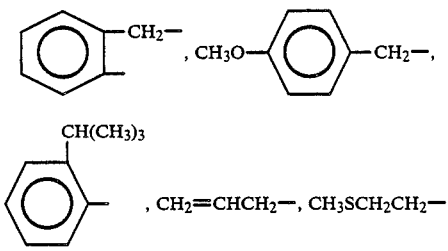

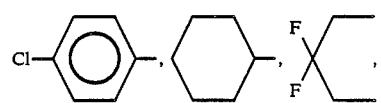

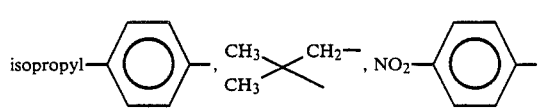

and $C_2H_5SO_2CH_2CH_2$—.

These reagents are either commercially available or are synthesized according to L. A. Slotin, Synthesis, 737 (1977); K. Sasse in Houben-Weyl, Methoden der Organischen Chemie, 4th Edition, Vol. XII/2, E. Muller Ed., Georg Thieme Verlag Stuttgart (1964); R. N. Hunston, et al., J. Med. Chem., 27, 440 (1984); P. Halvary and J. Weller, Helv. Chim. Acta., 69, 1862 (1986).

TABLE III
| Starting Material | Phosphate-Phosphonate |
|---|---|
| 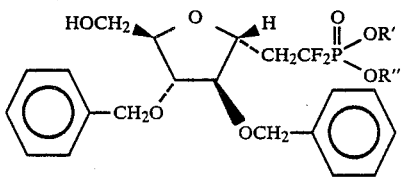 XII | 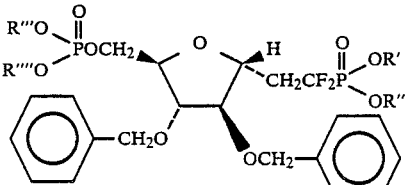 XX |
| 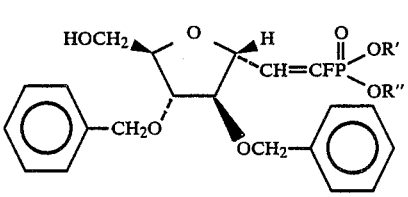 XIII | 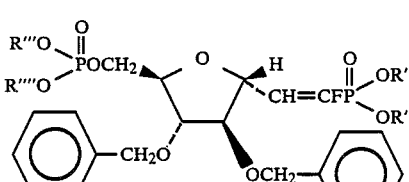 XXI |
| 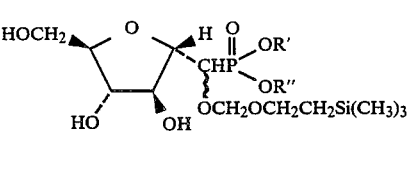 XIV | 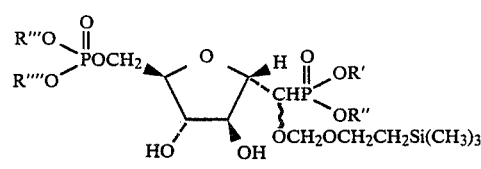 XXII |
| 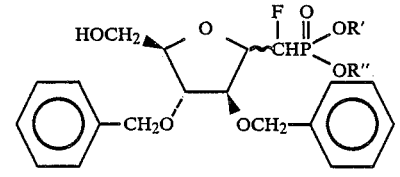 XV | 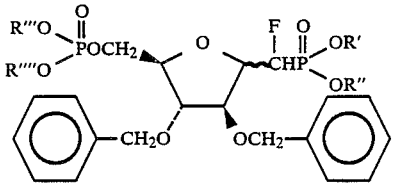 XXIII |
| 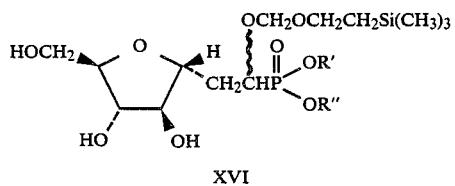 XVI | 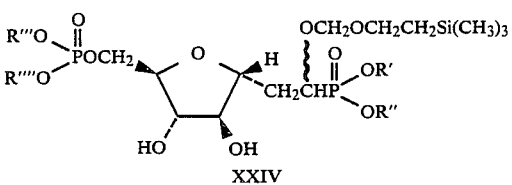 XXIV |
| 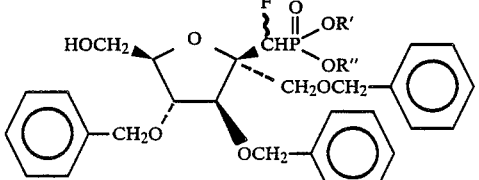 XVII | 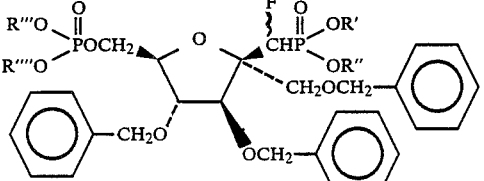 XXV |
| 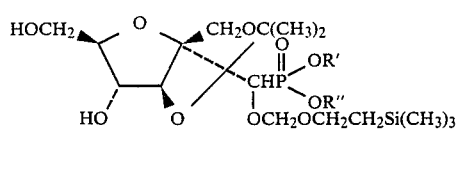 XVIII | 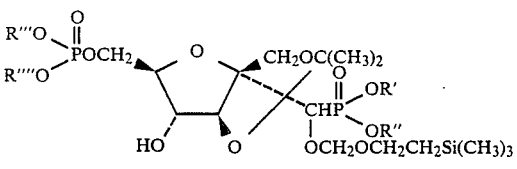 XXVI |

TABLE III-continued

| Starting Material | Phosphate-Phosphonate |
|---|---|
| 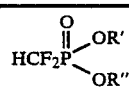 XIX | 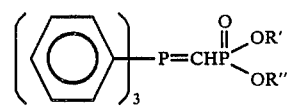 XXVII |

The phosphate-phosphonate compounds XX–XXVII may then be deprotected by the procedures of Examples 9 or 21 to provide the tetraesters of Formula I, where R', R", R''' and R'''' may be the same or different and are any of those substituents listed for R', R" in Tables IV–VIII.

TABLE IV $$HCF_2P\begin{matrix}O\\\|\end{matrix}\begin{matrix}OR'\\OR''\end{matrix}$$

| R', R" | References |
|---|---|
| Phenyl | M. Obayashi, et al., Tetrahedron Letters, 23, 2323(1982). L. Z. Soborovskii and N. F. Baina, J. Gen. Chem. U.S.S.R., 29, 1115(1959). K. Sasse, in: Houben-Weyl, Methoden der Organischen Chemie, 4th Edn., Vol. XII/2, E. Muller, Ed., Georg Thieme Verlag, Stuttgart (1964). |
| y—⌬— (y = alkyl, alkoxy, halo); alkyl (C$_1$–C$_8$) (straight or branched); cyclo-alkyl (C$_3$–C$_6$); W—CH$_2$CH$_2$— (W=CH$_2$S, halo); R' \| = —CH$_2$CH$_2$CH$_2$— R" | |

TABLE V $$HCF\left[\begin{matrix}O\\\|\\P\end{matrix}\begin{matrix}OR'\\OR''\end{matrix}\right]_2$$

| R', R" | References |
|---|---|
| alkyl (C$_1$–C$_8$) (straight or branched; cycloalkyl (C$_3$–C$_6$); R' \| = —CH$_2$CH$_2$CH$_2$— R" | K. Sasse (vide supra). C. E. McKenna, P. Shen, J. Org. Chem., 4573 (1981). M. Blackburn, et al., J. Chem. Soc. Chem Commun. 930 (1981). J. A. Cade, J. Chem. Soc. 2266 (1959). C. H. Roy, U.S. Pat. No. 3,251,907. |

TABLE VI $$HP\begin{matrix}O\\\|\end{matrix}\begin{matrix}OR'\\OR''\end{matrix}$$

| R',R" | References |
|---|---|
| Phenyl | Commercially available, or K. Sasse (vide supra). |
| 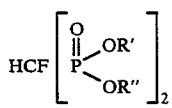 (y = alkoxy, alkyl, halo); alkyl (C$_1$–C$_8$) (straight or branched); Cycloalkyl (C$_3$–C$_6$); W—CH$_2$CH$_2$— (W=CH$_2$S, halo); | |

TABLE VI-continued $$HP\begin{matrix}O\\\|\end{matrix}\begin{matrix}OR'\\OR''\end{matrix}$$

| R',R" | References |
|---|---|
| R' \| = —CH$_2$CH$_2$CH$_2$— R" | |

TABLE VII $$\left(\bigcirc\right)_3 P=CHP\begin{matrix}O\\\|\end{matrix}\begin{matrix}OR'\\OR''\end{matrix}$$

| R',R" | References |
|---|---|
| Phenyl | K. Sasse (vide supra). |
| 2-Methylphenyl | G. H. Jones, et al., Tetrahedron Letters, 5731 (1968). |
| 3,5-Dimethylphenyl | |
| y—⌬— (y = alkyl, alkoxy, halo) | |

TABLE VIII $$HCH\left[\begin{matrix}O\\\|\\P\end{matrix}\begin{matrix}OR'\\OR''\end{matrix}\right]_2$$

| R', R" | References |
|---|---|
| Phenyl | Commercially available, or synthesized by a combination of methods in K. Sasse; J. A. Cade; and C. H. Roy (vide supra). |
| 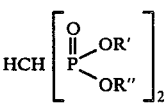 (y = alkoxy,alkyl,halo); alkyl (C$_1$–C$_8$) (straight or branched); cyclo-alkyl (C$_3$–C$_8$) W—CH$_2$CH$_2$— (W =CH$_2$S, halo) R' \| = —CH$_2$CH$_2$CH$_2$— R" | |

Alternatively, the free acids XXVIII–XXXVI in Table IX can be aklylated using a suitable diazo reagent, such as CH$_2$N$_2$, CH$_3$CHN$_2$, (CH$_3$)$_2$CN$_2$ or Ph-CHN$_2$, in anhydrous methanol at 0°–5° C., followed by the addition of acetic acid, evaporation and purification by chromotography, giving the tetraesters shown in Table IX, where each of the ester substituents are the same in the resulting tetraesters. In Table IX, the portion of the diazo reagents listed above which is incorporated into the tetraesters is indicated by the letter D.

TABLE IX

| Free Acid | Tetraester |
|---|---|
| XXVIII | |
| XXIX | |
| XXX | |
| XXXI | |
| XXXII | |
| XXXIII | |
| XXXIV | |
| XXXV | |

TABLE IX-continued

| Free Acid | Tetraester |
|---|---|
| (HO)$_2$—POCH$_2$—[ring]—CH$_2$OH, CHP—(OH)$_2$, HO, OH, F  XXXVI | (DO)$_2$—POCH$_2$—[ring]—CH$_2$OH, CHP—(OD)$_2$, HO, OH, F |

The diazo reagents may be prepared according to K. Sasse (vide supra); K. Bruzik and M.-D. Tsai, J. Am. Chem. Soc., 106, 747 (1984); or Fieser and Fieser, Reagents for Organic Synthesis. Volumes 1 and 2, Wiley Interscience.

The novel compounds of this invention were tested for their ability to stimulate the enzyme 6-phosphofructo-1-kinase ("PFK") and for their ability to inhibit the enzyme fructose-1,6-bisphosphatase ("FBP") using the procedures described below.

Effects on the activity of PFK were determined using an aldolase-coupled, spectrophotometric assay. The assay mixture contained: 50 mM N-tris(hydroxymethyl)methyl-2-aminoethanesulfonic acid, hydrochloride ("TES-HCl", pH 7.3); 1 mM ethylenediaminetetraacetic acid ("EDTA"); 6 mM magnesium chloride; 2.5 mM dithiothreitol; 0.165 mM nicotinamide adenine dinucleotide ("NADH"); 1 mM adenosine triphosphate ("ATP"); 0.04U aldolase; 0.4U triose phosphate isomerase; 1.5U alpha-glycerolphosphate dehydrogenase; 0.1U of purified rat liver 6-phosphofructo-1-kinase; and various concentrations of the test compound, all in a final volume of 1 ml. The mixture was preincubated for 3 minutes at 30° C. and then the reaction was initiated with 0.2 mM fructose-6-phosphate. The rate of decrease in absorbance at 340 nm was measured at 30° C. with a recording spectrophotometer.

Effects on the activity of FBP were determined using a spectrophotometric assay. The assay mixture contained: 100 mM tris(hydroxymethyl)aminomethane, hydrochloride ("TRIS-HCl", pH 7.4); 2.5 mM beta-mercaptoethanol; 2 mM magnesium chloride; 0.05 mM EDTA; 0.2 mM nicotinamide adenine dinucleotide phosphate ("NADP"); 10 U phosphoglucose isomerase; 5 U glucose-6-phosphate dehydrogenase; 0.02U of purified rat liver FBP; and various concentrations of the test compound, all in a final volume of 1 ml. The mixture was preincubated for 3 minutes at 30° C. and then the reaction was initiated with 0.02 mM fructose-1,6-bisphosphate. The rate of increase in absorbance at 340 nm was measured at 30° C. with a recording spectrophotometer The results of these tests on representative compounds of this invention are shown in Table X.

TABLE X

| Compound | PFK ED$_{50}$ ($\mu$M) | FBP IC$_{50}$ ($\mu$M) |
|---|---|---|
| Beta-D-fructose-2,6-bisphosphate (control) | 0.02 | 3 |
| 2,5-Anhydro-1-deoxy-1-fluoro-1-phosphono-D-mannitol, 6-(dihydrogen phosphate) | 22 | 114 |
| 2,5-Anhydro-1-deoxy-1-fluoro-1-phosphono-D-glucitol (and D-mannitol), 6-(dihydrogen phosphate) | 10 | 54 |
| [1R(and 1S)]-3,6-Anhydro-1,2-dideoxy-1-fluoro-1-phosphono-D-manno-heptitol, 7-(dihydrogen phosphate) | 1.3 | 61 |
| [1R(and/or 1S)]-3,6-Anhydro-2-deoxy-1-phosphono-D-manno-heptitol, 7-(dihydrogen phosphate) | 1.0 | 62 |
| 3,6-Anhydro-1,2-dideoxy-1,1-difluoro-1-phosphono-D-manno-heptitol, 7-(dihydrogen phosphate) | 3 | 27 |
| [1R(and/or 1S)]-2,5-Anhydro-1-C-phosphono-D-mannitol, 6-(dihydrogen phosphate) | 13 | 44 |
| 2,5-Anhydro-1-deoxy-1-fluoro-2-(hydroxymethyl)-1-phosphono-D-glucitol, 6-(dihydrogen phosphate) | 0.7 | 110 |
| 2,5-Anhydro-2-C-(fluorophosphonomethyl)-D-glucitol, 6-(dihydrogen phosphate) | 1.3 | 378 |
| 2,5-Anhydro-2-C-(hydroxyphosphonomethyl)-D-glucitol, 6-(dihydrogen phosphate) | 20 | 393 |
| 2,5-Anhydro-1-deoxy-1-difluoro-1-phosphono-D-mannitol, 6-(dihydrogen-phosphate) | 14 | 226 |

Although the naturally-occurring control compound had more in vitro activity, the compounds of this invention are more stable, so that they will provide more efficacious control over the glycolytic and gluconeogenic processes in mammals.

The compounds of Formulae I and II are normally administered to mammals in the form of their tetraesters, that is, where R', R", R''' and R'''' are C$_1$ to C$_6$ alkyl, C$_3$ to C$_6$ cycloalkyl or phenyl. The esters, being more lipophilic than the acids (R', R", R''' and R''''=H), pass through the mammalian cell wall more readily.

When the compounds of the present invention are employed for the above described utility, they may be combined with one or more pharmaceutically acceptable carriers such as solvents, diluents and the like, and may be administered in such forms as tablets, capsules, dispersible powders, granules or suspensions containing, for example, from about 0.5 to 5.0% of suspending agent, syrups containing, for example, from about 10 to 50% of a carrier, and elixirs containing, for example, from about 20 to 50% of ethanol, and the like, or parenterally in the form of sterile injectable solutions or suspensions containing from about 0.5 to 5 0% suspending agent in isotonic medium. These pharmaceutical preparations may contain, for example, from about 0.5 to 90.0% of the active ingredient in combination with the carrier, more usually between 5.0 and 60.0% by weight.

The effective dosage of active ingredient employed may vary depending on the particular compound, the mode of administration and the severity of the conditions being treated. However, in general, satisfactory results are obtained when the compounds of this invention are administered at a daily dosage of from about 1 mg to about 50 mg per kg of body weight, preferably given in divided doses two to four times daily or in sustained release form. Dosage forms suitable for internal use comprise from about 1 mg to about 50 mg of the active compound in intimate admixture with a solid or liquid pharmaceutically acceptable carrier. This dosage regimen may be adjusted to provide the optimal therapeutic response. For example, several divided doses may be administered daily or the dose may be proportionally reduced as indicated by the exigencies of the therapeutic situation. The compounds may be administered by a variety of routes including oral, intravenous, intramuscular and subcutaneous. Solid carriers include starch, lactose, dicalcium phosphate, microcrystalline cellulose, and kaolin; while liquid carriers include sterile water, polyethylene glycols, non-ionic surfactants and edible oils such as corn, peanut and sesame oils, as appropriate to the nature of the active ingredient and the particular form of administration desired. Adjuvants customarily employed in the preparation of pharmaceutical compositions may be advantageously included, such as flavoring agents, coloring agents, preservatives and antioxidants, e.g., vitamin E, ascorbic acid, butylated hydroxytoluene, and the like.

The preferred pharmaceutical compositions in terms of ease of preparation are solid compositions, particularly tablets and hard-filled or liquid-filled capsules. Oral administration of the compounds is preferred. These compounds may, however, be administered parenterally or intraperitoneally. Solutions or suspensions of the active compounds can be prepared in water suitably mixed with a surfactant such as hydroxypropylcellulose. Dispersions can also be prepared in glycerol, liquid polyethylene glycols, and mixtures thereof in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparations of sterile injectable solutions or dispersions. In all cases, the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, a polyol such as glycerol, propylene glycol or liquid polyethylene glycol, suitable mixtures thereof, or vegetable oils.

The invention will be more fully described in conjunction with the following specific examples which are not to be construed as limits thereon.

EXAMPLE 1

2,5-Anhydro-D-mannose, dimethyl acetal 2,5-Anhydro-D-mannose, made by the procedure of D. A. Otero & R. Simpson, Carbohydrate Res., 128, 79–86 (1984), was dissolved in 400 ml of anhydrous methanol and treated with 18 ml of acetyl chloride. The solution was heated at reflux for 3 hours, then neutralized with lead carbonate, filtered and the filtrate concentrated. The resulting oil was purified by chromatography, giving 14.9 g of the desired compound.

EXAMPLE 2

2,5-Anhydro-3,4,6-tris-O-(ohenvlmethvl)-D-mannose, dimethyl acetal

A 3.14 g portion of 2,5-anhydro-D-mannose, dimethyl acetal was dissolved in 120 ml of dry dimethylformamide and treated with 2.46 g of sodium hydride. The suspension was stirred for 1 hour, then 16.6 ml of benzyl bromide was added and the mixture was stirred overnight, providing 6.0 g of the desired compound after chromatography.

EXAMPLE 3

2,5-Anhydro-3,4,6-tris-O-(phenylmethyl)-D-mannose

A 790 mg portion of 2,5-anhydro-3,4,6-tris-O-(phenylmethyl)-D-mannose, dimethyl acetal was dissolved in 25 ml of acetonitrile and treated with 3.3 ml of 48% aqueous tetrafluoroboric acid. After 20 minutes the reaction was quenched with solid sodium bicarbonate. The solvent was removed and the residue extracted with ether, giving 730 mg of a yellow oil. This oil was flash chromatographed, eluting with hexane:ethyl acetate, giving 530 mg of the desired compound.

EXAMPLE 4

3,6-Anhydro-1-deoxy-1-(diethoxyohosohinyl)-1,1-difluoro-4,5,7-tris-O-(phenylmethyl)-D-glycero-D-galacto-heptitol, and
2,5-anhydro-7-deoxy-7-(diethoxyphosphinyl)-7,7-difluoro-1,3,4-tris-O-(phenylmethyl)-D-glycero-D-manno-heptitol Lithiodiisopropylamine was prepared as follows:

A solution of 1.15 ml of diisopropylamine in 10 ml of tetrahydrofuran was placed in a two necked, predried flask under an argon atmosphere and cooled to −75° C. in a dry ice-acetone bath. A 3.45 ml portion of n-butyl lithium was added over 5 minutes. The resulting solution was stirred for 30 minutes at −75° to −50° C., then placed in a 0° C. bath for 5 minutes, then recooled to −75° C.

A solution of 1.53 g of (difluoromethyl) phosphonic acid, diethyl ester in 2.1 ml of dry tetrahydrofuran was added to the solution of lithiodiisopropylamine over 5 minutes and the solution stirred at −75° C. for 15 minutes. To this was added a solution of 950 mg of 2,5-anhydro-3,4,6-tris-O-(phenylmethyl)--D-mannose in 3 ml of tetrahydrofuran. The solution was stirred for 1 hour at −70° C., then allowed to warm to −10° C. over a period of 1 hour, then recooled to −70° C. and quenched with 690 μl of acetic acid. The solution was warmed to room temperature, diluted with ether and ice and the layers separated. The organic layer was washed with cold 1N hydrochloric acid and water, then dried and evaporated, giving 1.90 g of a mixture of the desired compounds as an orange oil.

EXAMPLE 5

3,6-Anhydro-1-deoxy-1-(diethoxyphosphinyl)-1,1-difluoro-4,5,7-tris-O-(phenylmethyl)-D-glycero-D-galacto-heptitol, 0-1H-imidazole-1-carbothioate, and 2,5-anhvdro-7-deoxy-7-(diethoxyphosphinyl)-7,7-difluoro-1,3,4-tris-O-(phenylmethyl)-D-glycero-D-manno-heptitol and 284 mg of N,N'-thiocarbonyldiimidazole were dissolved heptitol, O-1H-imidazole-1-carbothioate A 437 mg portion of a mixture of 3,6-anhydro-1-deoxy-1-(diethoxyphosphinyl)-1,1-difluoro-4,5,7-tris-O-(phenylmethyl)-D-glycero-D-galacto-heptitol, and 2,5-anhydro-7-deoxy-7-(diethoxyphosphinyl)-7,7-difluoro-1,3,4-tris-O-(phenylmethyl)-D-glycero-D-manno-heptitol and 284 mg of N,N'-thiocarbonyldiimidazole were dissolved in 3.5 ml of dry tetrahydrofuran and stirred for 24 hours. The solvent was removed and the residual orange oil purified by flash chromatography eluting 30 ml fractions with hexane:ethyl acetate (1:1). Fractions 11–16 were combined and evaporated, giving 227 mg of the D-glycero-D-qalacto derivative. Fractions 21–27 were combined and evaporated, giving 36 mg of the D-glycero-D-manno derivative.

EXAMPLE 6

3,6-Anhydro-1,2-dideoxy-1-(diethoxyphosphinyl)-1,1-difluoro-4,5,7-tris-O-(phenylmethyl)-D-manno-heptitol A 440 mg portion of a mixture of 3,6-anhydro-1-deoxy-1-(diethoxyphosphinyl)-1,1-difluoro-4,5,7-tris-O-(phenylmethyl)-D-glycero-D-galacto-heptitol, O-1H-imidazole-1-carbothioate and 2,5-anhydro-7-deoxy-7-(diethoxyphosphinyl)-7,7-difluoro-1,3,4-tris-O-(phenylmethyl)-D-glycero-D-manno-heptitol, O-1H-imidazole-1-carbothioate was dissolved in 12 ml of dry toluene, then treated with 900 μl of n-tributyl stannous hydride and a few crystals of 2,2'-azobisisobutyronitrile and heated in an oil bath under argon for 3 hours. The solution was cooled, then stored in a freezer and finally evaporated. The resulting oil was purified by chromatography giving the desired compound.

EXAMPLE 7

3,6-Anhvdro-1 2-dideoxy-1-(diethoxyphsophinyl)-1.1-difluoro-4,5-bis-O-(phenylmethyl)-D-manno-heptitol A solution of 250 mg of 3,6-anhydro-1,2-dideoxy-1-(diethoxyphosphinyl)-1,1-difluoro-4,5,7-tris-O-(phenylmethyl)-D-manno-heptitol in 720 μl of acetic anhydride was cooled and treated with 75 μl of boron trifluoride etherate. After 50 minutes at 0° C., 0.5 ml of saturated sodium bicarbonate was added and the mixture was warmed to room temperature. Extraction with ether gave 250 mg of a yellow oil. This oil was dissolved in 1 ml of ethanol and treated with 110 μl of freshly prepared sodium ethoxide under an argon atmosphere. After 1 hour 75 μl of acetic acid was added and the volatiles removed. The residue was taken up in ether/saturated sodium bicarbonate. The ether layer was evaporated giving 186 mg of the desired compound as a yellowish oil.

EXAMPLE 8

3,6-Anhydro-1,2-dideoxy-1-(diethoxyphsophinyl)-1,1-difluoro-3,4-bis-O-(phenylmethyl)-D-manno-heptitol, 7-(diphenyl phosphate)

A 174 mg portion of 3,6-anhydro-1,2-dideoxy-1-(diethoxyphosphinyl)-1,1-difluoro-4,5-bis-O-(phenylmethyl)-D-manno-heptitol in 1.0 ml of pyridine was treated with 127 μl of diphenyl chlorophosphate while cooled in an ice bath under argon. After 30 minutes the mixture was refrigerated for 20 hours, then treated with a few drops of water, warmed to room temperature and evaporated. The residue was taken up in ether, washed with water, cold 1N hydrochloric acid, saturated sodium bicarbonate and brine, then dried and evaporated. The resulting oil was purified by flash chromatography, eluting 15 ml fractions with hexane:ethyl acetate. Fractions 9–16 were combined and evaporated, giving 160 mg of the desired compound.

EXAMPLE 9

3,6-Anhydro-1,2-dideoxy-1-(diethoxyohosphinyl)-1,1-difluoro-D-manno-heptitol, 7-(diphenyl phosphate)

A solution of 160 mg of 3,6-anhydro-1,2-dideoxy-1-(diethoxyphosphinyl)-1,1-difluoro-3,4-bis-O-(phenylmethyl)-D-manno-heptitol, 7-(diphenyl phosphate) and palladium oxide in methanol was hydrogenated until the uptake of hydrogen ceased. The mixture was filtered and the filtrate evaporated. The resulting oil was purified by flash chromatography, eluting 20 ml fractions with 4% methanol in dichloromethane. Fractions 5–10 were combined and evaporated, giving 98 mg of the desired product.

EXAMPLE 10

3,6-Anhydro-1,2-dideoxy-1,1-difluoro-1-phosphono-D-manno-heptitol, 7-(dihydrogen phosphate)

A solution of 95 mg of 3,6-anhydro-1,2-dideoxy-1-(diethoxyphosphinyl)-1,1-difluoro-D-manno-heptitol, 7-(diphenyl phosphate) in 800 μl of deuterated chloroform was degassed with argon and treated with 100 μl of trimethylsilyl bromide under an argon atmosphere. After 10 hours the mixture was refrigerated, then returned to room temperature and evaporated. The residue was evaporated twice from acetone and water, giving 94 mg of 3,6-anhydro-1,2-dideoxy-1,1-difluoro-1-phosphono-D-manno-heptitol, 7-(diphenyl phosphate).

The above 94 mg was dissolved in 18 ml of methanol and hydrogenated over platinum oxide at 60 psi for 1.5 hours. Filtration and removal of the solvent gave 78 mg of the desired product as a colorless oil.

EXAMPLE 11

(E)-3,6-Anhvdro-1,2-dideoxy-1-(diethoxyphosphinyl)-1-fluoro-4,5,7-tris-0-(phenylmethyl)-D-manno-hept-1-enitol A solution of 450 mg of tetraethyl difluoromethylene diphosphonate in 0.86 ml of ether was cooled in an ice/salt bath and treated with 0.78 ml of 2.1M n-butyl lithium. Stirring was continued at 0° C. for 10 minutes, then at room temperature for 50 minutes, then the mixture was recooled to 0° C. A 640 mg portion of 2,5-anhydro-3,4,6-tris-O-(phenylmethyl)-D-mannose prepared in accordance with Examples 1–3 was dissolved in 2.3 ml of ether and added to the cold reagent over 5 minutes. Stirring was continued at 0° C. for 25 minutes, then at room temperature for 1 hour. The reaction was quenched with water. The aqueous phase was extracted four times with ether. The ether solutions were combined, washed with brine, dried and evaporated. The residue was purified by flash chromatography, eluting 40 ml fractions with hexane:ethyl acetate (3:1). Fractions 19–33 were combined and evaporated giving 610 mg of the desired compound.

EXAMPLE 12

(E)-3,6-Anhydro-1,2-dideoxy-1-(diethoxyphsophinyl)-1-fluoro-4,5-bis-O-(phenylmethyl)-D-manno-hept-1-enitol A 533 mg portion of (E)-3,6-anhydro-1,2-dideoxy-1-(diethoxyphosphinyl)-1-fluoro-4,5,7-tris-O-(phenylmethyl)-D-manno-hept-1-enitol was dissolved in 1.4 ml of acetic anhydride and this solution was cooled in an ice/salt bath. A 1.2 ml portion of boron trifluoride etherate was added. After stirring for 50 minutes, 0.95 ml of saturated sodium bicarbonate solution was added and the mixture was stirred at room temperature for 15 minutes. Ether workup gave 525 mg of a yellow oil.

This oil was dissolved in 2.3 ml of ethanol and treated with 212 μl of freshly prepared sodium ethoxide. After 40 minutes 110 μl of glacial acetic acid was added and the solution was evaporated. The residue was taken up in ether, washed with saturated sodium bicarbonate solution, brine, dried and evaporated. The resultant oil was purified by flash chromatography, eluting 30 ml fractions with hexane:ethyl acetate (1:1), giving 400 mg of the desired compound.

EXAMPLE 13

(E)-3,6-Anhydro-1,2-dideoxy-1-(diethoxyphosphinyl)-1-fluoro-4,5-bis-O-(phenylmethyl)-D-manno-hept-1-enitol, 7-(diphenyl phosphate)

A 358 mg portion of (E)-3,6-anhydro-1,2-dideoxy-1-(diethoxyphosphinyl)-1-fluoro-4,5-bis-O-(phenyl- methyl)-D-manno-hept-1-enitol was dissolved in 2 ml of pyridine in an ice bath. A 230 μl portion of diphenyl chlorophosphate was added, the mixture refrigerated overnight, then warmed to room temperature, treated with a few drops of water and evaporated. The residue was taken up in ether, washed with water, cold 1N hydrochloric acid, saturated copper sulfate and brine, dried and evaporated. The residue was purified by flash chromatography, eluting 25 ml fractions with hexane:ethyl acetate (2:1). Fractions 13–33 Were combined and evaporated, giving 440 mg of the desired compound.

EXAMPLE 14

[1R(and 1S)]-3,6-Anhydro-1,2-dideoxy-1-(diethoxyphosphinyl)-1-fluoro-D-manno-heptitol, 7-(diphenyl phosphate)

A 397 mg portion of (E)-3,6-anhydro-1,2-dideoxy-1-(diethoxyphosphinyl)-1-fluoro-4,5-bis-O-(phenylmethyl)-D-manno-hept-1-enitol, 7-(diphenyl phosphate) was dissolved in 20 ml of methanol and hydrogenated over palladium on carbon until hydrogen uptake ceased. The mixture was filtered and the filtrate evaporated. The residue was purified by flash chromatography, eluting 25 ml fractions with 5% methanol in dichloromethane. Fractions 5–17 were combined and evaporated, giving 270 mg of the desired product.

EXAMPLE 15

(1R)-3,6-Anhydro-1,2-dideoxy-1-fluoro-1-phosphono--D--manno-heptitol, 7-(diphenyl phosphate) and (1S)-3,6--Anhydro-1,2-dideoxy-1-fluoro-1-phosphono-D-manno-heptitol, 7-(diphenyl phosphate)

A 258 mg portion of [1R(and 1S)]-3,6-anhydro--1,2-dideoxy-1-(diethoxyphosphinyl)-1-fluoro-D-mannoheptitol, 7-(diphenyl phosphate) was dissolved in 2.3 ml of deuterated chloroform and treated with 194 μl of trimethylsilyl bromide under an argon atmosphere. After standing 12 hours, the mixture was evaporated. The residue was evaporated twice from acetone/water, giving 253 mg of the desired product.

EXAMPLE 16

(1R)-3,6-Anhvdro-1,2-dideoxy-1-fluoro-1-phosphono--D--manno-heptitol, 7-(dihydrogen phosphate) mixture with (1S)-3,6-Anhydro-1,2-dideoxy-1-fluoro-1-phosohono--D--manno-heptitol, 7-(dihydrogen phosphate)

A solution of 243 mg of a mixture of (1R) and (1S)-3,6-anhydro-1,2-dideoxy-1-fluoro-1-phosphono-D-manno-heptitol, 7-(diphenyl phosphate) in 25 ml of methanol was hydrogenated over platinum oxide catalyst until hydrogen uptake ceased. The mixture was filtered and the solvent removed, giving 160 mg of the desired product as a colorless oil.

EXAMPLE 17

[1R(and/or 1S)]-2,5-Anhydro-1-C-(diethoxyphosphinyl)--3,4,6-tris-O-(ohenvlmethvl)-D-qlucitol A 1.52 g portion of 2,5-anhydro-3,4,6-tris-O-(phenylmethyl)-D-mannose, prepared in accordance with Examples 1–3, was placed in a round bottom flask, flushed with argon and dissolved in 2.253 ml of diethyl phosphite. This mixture was treated with 140 μl of sodium ethoxide and stirred at room temperature under argon. After 20 minutes, 200 μl of diethyl phosphite and 40 μl of sodium ethoxide were added and stirring continued. The mixture was taken up in ice and the flask rinsed with ether. The ether layer was separated and evaporated. The residue was purified by flash chromatography, eluting 75 ml fractions with hexane:ethyl acetate (1:1). Fractions 9–21 were combined and evaporated, giving 1.59 g of the desired compound.

EXAMPLE 18

[1R(and/or 1S)]-2,5-Anhydro-1-C-(diethoxvohosphinvl)-3,4,6-tris-O-(phenylmethyl)-1-O-[[2-(trimethvlsilyl)-ethoxy]methyl]-D-mannitol A 623 mg portion of [1R(and/or 1S)]-2,5-anhydro-1-C-(diethoxyphosphinyl)-3,4,6-tris-O-(phenylmethyl)-D-glucitol was dissolved in 968 μl of dry dichloromethane and then treated with 775 μl of N,N-diisopropylethylamine and 496 μl of 2-(trimethylsilyl)ethoxymethyl chloride, under argon at room temperature. After 15 minutes, the mixture was heated and stirred at 40°–50° C. with a reflux condenser for 3 hours, then 311 μl of methanol were added and the solvent evaporated. The residue was taken up in water and toluene. The aqueous phase was washed twice with toluene. The combined toluene solutions were washed with saturated sodium bicarbonate and brine, dried and evaporated to an oil. This oil was purified by flash chromatography, eluting 40 ml fractions with hexane:ethyl acetate (2:1). Fractions 9–17 were combined and evaporated, giving 647 mg of the desired compound.

EXAMPLE 19

[1R(and/or 1S)]-2,5-Anhvdro-1-C-(diethoxyphosphinyl)-1-O-[[2-(trimethylsilyl)ethoxy1methyl1-D-mannitol A 647 mg portion of [1R(and/or 1S)]-2,5-anhydro-1-C-(diethoxyphosphinyl)-3,4,6-tris-0-(phenylmethyl)-1-O-[[2-(trimethylsilyl)ethoxy]methyl]-D-mannitol was dissolved in 20 ml of dry methanol and hydrogenated over palladium hydroxide on carbon until the uptake of hydrogen ceased. The mixture was filtered and the solvent removed, giving an oil. This oil was purified by flash chromatography, eluting 25 ml fractions with 5% methanol in dichloromethane. Fractions 7-12 were combined and evaporated, giving 242 mg of the desired compound.

EXAMPLE 20

[1R(and/or 1S)-2,5-Anhvdro-1-C-(diethoxyphosphinyl)-1-O-[[2-(trimethylsilyl)ethoxy]methyl]-D-mannitol, 6-(diphenyl phosphate)

A 314 mg portion of [1R(and/or 1S)]-2,5-anhydro-1-C-(diethoxyphosphinyl)-1-O-[[2-(trimethylsilyl)ethoxy]methyl]-D-mannitol was dissolved in 2.1 ml of pyridine cooled in an ice bath. A 231 $\mu$l portion of diphenyl chlorophosphate was added dropwise. This mixture was stirred ½ hour, refrigerated overnight, then treated with 100 $\mu$l of water, stirred 10 minutes, warmed to room temperature and evaporated. The residue was taken up in dichloromethane, washed with water, cold 1N hydrochloric acid and saturated sodium bicarbonate, dried and evaporated. The resultant oil was purified by flash chromatography, eluting 25 ml fractions with dichloromethane:ether:methanol (8:2:0.1). Fractions 40-51 were combined and evaporated, giving 288 mg of the desired compound.

EXAMPLE 21

[1R(and/or 1S)1-2,5-Anhvdro-1-C-(diethoxyphsophinyl)-D-mannitol, 6-(diphenyl phosphate)

A 264 mg portion of [1R(and/or 1S)]-2,5-anhydro-1-C-(diethoxyphosphinyl)-1-O-[[2-(trimethylsilyl)ethoxy]methyl]-D-mannitol, 6-(diphenyl phosphate) was dissolved in 1.78 ml of anhydrous acetonitrile under argon and treated with 98 $\mu$l of boron trifluoride etherate. This mixture was stirred for 5 hours, then poured over 5 g of ice and extracted three times with dichloromethane, then twice with ether. The organic extracts were combined, dried and evaporated. The residue was purified by flash chromatography, eluting 15 ml fractions with 4% methanol in dichloromethane. Fractions 11-20 were combined and evaporated, giving 156 mg of the desired product.

EXAMPLE 22

[1R(and/or 1S)1-2,5-Anhvdro-1-C-phosphono-D-mannitol, 6-(dihydroqen phosphate)

A 95 mg portion of [1R(and/or 1S)]-2,5-anhydro-1-C-(diethoxyphosphinyl)-D-mannitol, 6-(diphenyl phosphate) was dissolved in 900 $\mu$l of deuterated chloroform under argon. A 100 $\mu$l portion of bromotrimethylsilane was added. The mixture was stirred under argon for ½ hour then refrigerated overnight, stirred for 9.5 hours at room temperature and then refrigerated for 48 hours. The mixture was evaporated and then re-evaporated twice from acetone-water and dried, giving 102 mg of solid.

This solid was dissolved in 13 ml of methanol and hydrogenated over platinum oxide. When hydrogen uptake ceased, the mixture was filtered and the filtrate evaporated, giving 70 mg of the desired product as an oil

EXAMPLE 23

1,2-Dideoxy-1-(diethoxyphsophinyl)-1-fluoro-3,4,6-tris-O-(phenylmethyl)-D-arabino-hex-1-enitol A solution of lithiodiisopropylamine was prepared as described in Example 4 and cooled to $-75°$ C. A 1.7 g portion of (fluoromethyl)diphosphonic acid, diethyl ester in 1.5 ml of tetrahydrofuran was added. After 15 minutes at $-75°$ C., 826 mg of 2,3,5-tris-O-(phenylmethyl)-D-arabinofuranose (Sigma Chemical Co.) was added together with 0.5 ml of tetrahydrofuran. The mixture was allowed to warm to room temperature and was then purified by flash chromatography, eluting 50 ml fractions with hexane:ethyl acetate (2:1). Fractions 16-26 were combined and evaporated, giving 520 mg of the desired compound.

EXAMPLE 24

2,5-Anhydro-1-deoxy-1-(diethoxyphosphinyl)-1-fluoro-3,4,6-tris-O-(phenylmethyl)-D-qlucitol and D-mannitol mixture A 477 mg portion of 1,2-dideoxy-1-(diethoxyphosphinyl)-1-fluoro-3,4,6-tris-O-(phenylmethyl)-D-arabino-hex-1-enitol was dissolved in 3 ml of ethanol and treated with 100 $\mu$l of 2.5N sodium ethoxide in ethanol under argon After 3 hours, acetic acid was added and the mixture evaporated. The residue was taken up in ether/water. The ether layer was separated and evaporated. The resulting oil was purified by flash chromatography, eluting 30 ml fractions with hexane:ethyl acetate (2:1). Fractions 12-18 were combined and evaporated, giving 327 mg of the desired compounds as a mixture.

EXAMPLE 25

2,5-Anhydro-1-deoxy-1-(diethoxyphosphinyl)-1-fluoro-3.4-bis-O-(phenylmethyl)-D-glucitol and D-mannitol mixture A solution of 289 mg of 2,5-anhydro-1-deoxy-1-(diethoxyphosphinyl)-1-fluoro-3,4,6-tris-0-(phenylmethyl)-D-glucitol and D-mannitol mixture in 850 $\mu$l of acetic anhydride was cooled in an ice/salt bath and treated with 76 $\mu$l of boron trifluoride etherate After 40 minutes at 0° C., 16 $\mu$l of boron trifluoride etherate was added. After 1 hour and 20 minutes at 0° C., the solution was treated with 50 $\mu$l of saturated sodium bicarbonate and warmed to room temperature. Ether workup gave 300 mg of the acetate derivative as an oil.

The 300 mg of oil was dissolved in 1.5 ml of ethanol and treated with 140 $\mu$l of 2.2N sodium ethoxide under argon. After 20 minutes, 80 $\mu$l of acetic acid was added and the volatiles removed. Ether/sodium bicarbonate workup gave 260 mg of the desired compound

EXAMPLE 26

[2,5-Anhydro-1-deoxy-1-(diethoxyphosphinyl)-1-fluoro-3,4-bis-O-(phenylmethyl)-D-qlucitol and D-mannitol, diphenyl phosphate mixture A solution of 274 mg of 2,5-anhydro-1-deoxy-1-(diethoxyphosphinyl)-1-fluoro-3,4-bis-O-(phenylmethyl)-D-glucitol and D-mannitol mixture in 1.5 ml of pyridine was cooled in an ice bath under argon and treated with 208 $\mu$l of diphenyl chlorophosphate. After 30 minutes the mixture was refrigerated for 20 hours, then treated with a few drops of water, warmed to room temperature and evaporated. The residue was taken up in ether, washed with water, cold 1N hydrochloric acid, saturated sodium bicarbonate and brine, dried and evaporated The resultant oil was purified by flash chromatography, eluting 15 ml fractions with hexane:ethyl acetate (3:2). Fractions 8–21 were combined and evaporated, giving 360 mg of the desired compounds as a mixture.

EXAMPLE 27

2,5-Anhydro-1-deoxy-1-(diethoxyphosphinyl)-1-fluoro-D-flucitol, 6-(diphenyl phosphate) and 2,5-anhydro-1-deoxy-1-(diethoxyphosphinyl)-1-fluoro-D-mannitol,6-(diphenyl phosphate)

A solution of 330 mg of 2,5-anhydro-1-deoxy-1-(diethoxyphosphinyl)-1-fluoro-3,4-bis-O-(phenylmethyl)-D-glucitol D-glucitol and D-mannitol, diphenyl phosphate mixture in 20 ml of methanol was hydrogenated over palladium hydroxide catalyst until hydrogen uptake ceased. Filtration and removal of the solvent gave a yellow oil. This oil was purified by flash chromatography taking 20 ml fractions Fractions 1–26 were eluted with 3% methanol in dichloromethane and after evaporation gave 135 mg of 2,5-anhydro-1-deoxy-1-(diethoxyphosphinyl)-1-fluoro-D-mannitol, 6-(diphenyl phosphate).

Fractions 27–39 were eluted with 5% methanol in dichloromethane and after evaporation gave 68 mg of 2,5-anhydro-1-deoxy-1-(diethoxyphosphinyl)-1-fluoro-D glucitol and D-mannitol, 6-(diphenyl phosphate) in a 3:1 mixture.

EXAMPLE 28

2,5-Anhydro-1-deoxy-1-fluoro-1-phosohono-D-mannitol, 6-(dihydrogen phosphate)

A solution of 135 mg of 2,5-anhydro-1-deoxy-1-(diethoxyphosphinyl)-1-fluoro-D-mannitol, 6-(diphenyl phosphate) in 1.2 ml of deuterated chloroform was treated with 150 μl of trimethylsilyl bromide under argon. After 6 hours the mixture was stored in a refrigerator, then evaporated. The residue was treated with acetone and water giving 30 mg of solid.

The 30 mg of solid was hydrogenated in 15 ml of methanol over platinum oxide, giving 20 mg of the desired product as a colorless oil.

EXAMPLE 29

2,5-Anhydro-1-deoxy-1-fluoro-1-phosphono-D-glucitol and D-mannitol, 6-(dihydrogen phosphate) mixture (70:30)

A 60 mg portion of 2,5-anhydro-1-deoxy-1-(diethoxyphosphinyl)-1-fluoro-D-glucitol and D-mannitol, 6-(diphenyl phosphate) 3:1 mixture was treated with trimethylsilyl bromide as in Example 28, then dissolved in 13 ml of methanol and hydrogenated over platinum oxide, giving 40 mg of the desired product as a mixture.

EXAMPLE 30

(E)-3,6-Anhydro-1,2-dideoxy-1-(diphenoxyphosphinyl)-4,5,7-tris-O-(phenylmethyl)-D-manno-heptitol An 880 mg portion of 2,5-anhydro-3,4,6-tris-O-(phenylmethyl)-D-mannose, prepared in accordance with Examples 1–3, was dissolved in 6 ml of dry toluene and treated with 1.11 g of triphenylphosphoranylidinemethylphosphonate at reflux for 24 hours. The solution was filtered through magnesol which was then washed with ether until all of the product was removed from the filter and then evaporated to a brown oil. Flash chromatography, eluting with hexane:ethyl acetate (3.5:1) and taking 50 ml fractions gave 660 mg of the desired compound.

EXAMPLE 31

3,6-Anhydro-2-deoxy-1-C-(diphenoxyphosphinyl)-4,5,7-tris-O-(phenylmethyl)-D-glycero-D-galacto-heptitol and 2,5-Anhydro-6-deoxy-7-C-(diphenoxyphosphinyl)-1,3,4-tris-O-(phenylmethyl)-D-glycero-D-manno-heptitol A 342 mg portion of (E)-3,6-anhydro-1,2-dideoxy-1-(diphenoxyphosphinyl)-4,5,7-tris-O-(phenylmethyl)-D-manno-heptitol was dissolved in 3.5 ml of dry tetrahydrofuran and cooled in an ice/salt bath. A 1.65 ml portion of borane-tetrahydrofuran complex was added, after 5 minutes the ice bath was removed and the reaction proceeded at room temperature for 4.5 hours. The solution was recooled in the ice/salt bath and treated with 5.2 ml of cold 1N sodium hydroxide and 5.2 ml of 30% hydrogen peroxide After 5 minutes, the bath was removed, the mixture stirred at room temperature for 35 minutes and the volatiles removed. The aqueous phase was extracted three times with ether and twice with chloroform, the extracts combined, dried and evaporated to an oil. Flash chromatography of this oil, eluting 40 ml fractions with hexane:ethyl acetate (3.5:1), gave 200 mg of the desired compounds as a mixture.

EXAMPLE 32

[1R(and 1S)1-3,6-Anhydro-2-deoxy-1-C-(diphenoxyphosphinyl)-4,5,7-tris-O-(phenylmethyl)-1-O-[[2-(trimethylsilyl)ethoxy]methyl]-D-manno-heptitol A 385 mg portion of a mixture of 3,6-anhydro-2-deoxy-1-C-(diphenoxyphosphinyl)-4,5,7-tris-O-(phenylmethyl)-D-glycero-D-galacto-heptitol and 2,5-anhydro-6-deoxy-7-C-(diphenoxyphosphinyl)-1,3,4-tris-O-(phenylmethyl)-D-glycero-D-manno-heptitol was dissolved in 500 μl of dry dichloromethane and treated first with 371 mg of diisopropylethylamine and then with 300 mg of 2-(trimethylsilyl)ethoxymethyl chloride under an argon atmosphere. The mixture was stirred overnight, then heated at 40°–50° C. for 30 minutes, 20 ml of methanol added and the volatiles removed. The residue was taken up in water/toluene, the aqueous layer was separated, washed with toluene, the toluene solutions combined, washed with sodium bicarbonate, brine, dried and evaporated. The residue was purified by flash chromatography, eluting 30 ml fractions with hexane:ethyl acetate (4:1) then (2:1), giving, from fractions 5–8, 250 mg of the desired compound.

EXAMPLE 33

[1R(and 1S)]-3,6-Anhydro-2-deoxy-1-C-(diphenoxyphosphinyl)-1-O-[[2-(trimethylsilyl)ethoxy]methyl-D-manno-heptitol A 340 mg portion of [1R(and 1S)]-3,6-anhydro-2-deoxy-1-C-(diphenoxyphosphinyl)-4,5,7-tris-O-(phenylmethyl)-1-O-[[2-(trimethylsilyl)ethoxy]methyl]-D-manno-heptitol was dissolved in methanol and hydrogenated over palladium hydroxide. After 4.5 hours the mixture was filtered and the filtrate evaporated, giving 247 mg of the desired compound as a pale yellow oil.

EXAMPLE 34

[1R(and
1S)]-3,6-Anhydro-2-deoxy-1-C-(diphenoxyphosphinyl)-1-O-[[2-(trimethylsilyl)ethoxy]methyl]-D-manno-heptitol, 7-(diphenyl phosphate)

A 240 mg portion of dried [1R(and 1S)]-3,6-anhydro-2-deoxy-1-C-(diphenoxyphosphinyl)-1-O-[[2-(trimethylsilyl)ethoxy]methyl]-D-manno-heptitol was dissolved in 1.3 ml of pyridine at 0° C. and treated with 122 μl of diphenyl chlorophosphate. The mixture was stirred at 0° C. for 30 minutes, then refrigerated overnight. Work-up gave a yellow oil which was purified by flash chromatography, eluting 25 ml fractions with dichloromethane:methanol:ether (8.0:0.2:2.0), giving, from fractions 11–24, 169 mg of the desired compound.

EXAMPLE 35

[1R(and/or
1S)]-3,6-Anhydro-2-deoxy-1-C-(diphenoxyphosphinyl)-D-manno-heptitol, 7-(diphenyl phosphate)

A 92 mg portion of [1R(and 1S)]-3,6-anhydro-2-deoxy-1-C-(diphenoxyphosphinyl)-1-O-[[2-(trimethylsilyl) ethoxy]methyl]-D-manno-heptitol, 7-(diphenyl phosphate) was dissolved in 540 μl of anhydrous acetonitrile and treated with 16 μl of borontrifluoride etherate under argon for 1 hour, then poured over 5 g of ice and extracted three times with 3–5 ml of dichloromethane and twice with ether. The organic phases were combined, dried and the solvent removed. The crude product was purified by flash chromatography, eluting 10 ml fractions with 3% methanol in dichloromethane followed by 4% methanol in dichloromethane. Fractions 15–26 gave 53 mg of the desired product when combined and evaporated.

EXAMPLE 36

[1 R(and/or
1S)]-3,6-Anhydro-2-deoxy-1-phosphono-D-manno-heptitol, 7-(dihydrogen phosphate)

A 50 mg portion of [1R(and/or 1S)]-3,6-anhydro-2-deoxy-1-(diphenoxyphosphinyl)-D-manno-heptitol, 7-(diphenyl phosphate) was dissolved in 20 ml of methanol and hydrogenated over platinum oxide for 1.5 hours. Removal of the solvent after filtration gave 33 mg of the desired product.

EXAMPLE 37

2,5-Anhydro-2-C-(hydroxymethyl)-3,4,6-tris-O-(phenylmethyl)-D-arabino-hexitol

A 1.18 g portion of 2,5-anhydro-3,4,6-tris-O-(phenylmethyl)-D-mannose prepared in accordance with Examples 1–3 was dissolved in 8.5 ml of methanol, treated with 5.11 ml of 37% formalin and 480 mg of potassium carbonate and the mixture immersed in an 85° C. bath. After 4 hours the mixture was cooled, neutralized with 3.5 ml of 10% sulfuric acid and the volatiles removed. The residue was extracted with chloroform, giving 0.86 g of the desired compound after chromatography.

EXAMPLE 38

2,5-Anhydro-2-C-(hydroxymethyl)-3,4,6-tris-O-phenylmethyl)-1,2$^1$-O-(phenylmethylene)-[R(or S)]-glucitol A 1.40 g portion of 2,5-anhydro-2-C-(hydroxymethyl)-3,4,6-tris-O-(phenylmethyl)-D-arabino-hexitol, 568 μl of benzaldehyde dimethyl acetal, 2.1 ml of dry dimethylformamide and 10 mg of p-toluenesulfonic acid were placed in a 15 ml flask attached to a rotary evaporator. After rotating under aspirator pressure in a 60° C. bath for 1 hour, 0.5 ml of dimethylformamide and 50 μl of benzaldehyde dimethyl acetal were added. Stirring was continued at 60° C. for 30 minutes, then at 65° C. for 30 minutes followed by evaporation of the solvent at 90° C.. The residue was dissolved in chloroform and saturated aqueous sodium bicarbonate. The aqueous layer was washed with chloroform and the combined organic solution dried and evaporated giving 2 g of a yellow oil containing a mixture of the desired product and its epimer. The products were isolated by flash chromatography eluting with hexane:ethyl acetate (6:1), to yield 1.05 g of the less polar isomer (oil) and 235 mg of the more polar isomer (solid, m.p. 111°–112° C.) of the desired compound.

EXAMPLE 39

2,5-Anhydro-2-C-[(phenylmethoxy)methyl-2,4,6-tris-O-(phenylmethyl)-D-glucitol

A 4.30 g portion of 2,5-anhydro-2-C-(hydroxymethyl)-3,4,6-tris-O-(phenylmethyl)-1,2$^1$-O-(phenylmethylene)-[R(and S)]-glucitol, epimeric mixture (about 3:1, less polar:more polar) was dissolved in 34 ml of dichloromethane:ether (1:1) and added to a slurry of 973 mg of lithium aluminum hydride and 3.33 g of aluminum chloride in 54 ml of the same solvent. After 25 minutes at 45°–50° C. the reaction was quenched with 13.4 ml of ethyl acetate and 26.5 ml of water. Extraction in ether gave 4.64 g of an oil containing both the glucitol and mannitol products. The isomers were separated by flash chromatography, eluting with 0.5% methanol in dichloromethane, giving 2.90 g of the desired glucitol compound.

EXAMPLE 40

2,5-Anhydro-2-C-[(phenylmethoxy)methyl-3,4,6-tris-O-(phenylmethyl)-D-glucose

A solution of 6.04 ml of dimethyl sulfoxide in 17.4 ml of dichloromethane was added to a solution of 3.29 ml of oxalyl chloride in 8.9 ml of dichloromethane at −60° C. under argon. This mixture was stirred at −60° C. for 20 minutes, then 9.64 g of dried 2,5-anhydro-2-C-[(phenylmethoxy)methyl]-2,4,6-tris-O-(phenylmethyl)-D-glucitol in 17.4 ml of dichloromethane was added at −60° C. over 8 minutes. The mixture was allowed to warm to −20° C. over 30 minutes, stirred at −20° C. for 30 minutes, then recooled to −30° C. and 24.4 ml of triethylamine added. The cooling bath was removed after 10 minutes, 107 ml of water added, the mixture stirred at room temperature for 10 minutes and then worked up to give 10.1 g of a yellow oil. Flash chromatography, eluting 125 ml fractions with hexane:ethyl acetate (4:1) gave, from fractions 6–9, 8.5 g of the desired compound.

EXAMPLE 41

2,5 Anhydro-1-C-(diethoxyphosphinyl)-2-C-[(phenylmethoxy)methyl]-3,4,6-tris-O-(phenylmethyl)-D-glucitol A 7.20 g portion of 2,5-anhydro-2-C-[(phenylmethoxy)methyl]-3,4,6-tris-O-(phenylmethyl)-D-glucose was dissolved in 6.7 ml of phosphonic acid, diethyl ester and treated with 620 μl of triethylamine under argon. After 4.5 hours 800 μl of acetic acid was added, the resulting yellow oil taken up in ether, washed with water, saturated with hexane, rewashed with water, then twice with brine, dried and evaporated. The residual oil was flash chromatographed, eluting 75 ml fractions with ether:toluene (2:1).

Fractions 9–11 were combined to give 3.77 g of the major, less polar component, which is used in Example 42.

Fractions 12–20 gave 4.77 g of a mixture of components.

EXAMPLE 42

[1R(or 1S)]-2,5-Anhydro-1-deoxy-1-(diethoxyphosphinyl)-1-fluoro-2-C-(phenylmethoxy)methyl]-3.4.6-tris-O-(phenylmethyl-D-glucitol A solution of 2.9 g of the less polar component from Example 41 in 18 ml of dry dichloromethane was cooled in an ice/salt bath to −5° C. and treated with a total of 1.65 ml of diethylamino sulfur trifluoride in portions over a period of 3.1 hours with the bath temperature gradually adjusted from −5° to 8° to 12° to 20° to 5° C. A 16 ml portion of saturated sodium bicarbonate was added and the mixture stirred until effervescence ceased. The organic layer was separated, washed with brine, dried and evaporated. The residual oil was flash chromatographed twice, eluting 40 ml fractions with hexane:ethyl acetate (2:1), giving 180 mg of the desired compound.

EXAMPLE 43

2,5-Anhydro-1-deoxy-1-(diethoxyphosphinyl)-1-fluoro-2-C-(phenylmethoxy)methyl]-3.4-bis-O-(phenylmethyl)-D-glucitol, acetate A cold (°C.) solution of 835 mg of [1R(or 1S)]-2,5-anhydro-1-deoxy-1-(diethoxyphosphinyl)-1-fluoro-2-C-[(phenylmethoxy)methyl]-3,4,6-tris-O-(phenylmethyl)-D-glucitol in 1.8 ml of acetic anhydride was treated with 75 μl of boron trifluoride etherate, syringed directly into the reaction, followed by 75 μl of boron trifluoride etherate in 75 ml of cold acetic anhydride and, after 1 hour, 82 μl of boron trifluoride etherate, with stirring under argon. The mixture was stirred 35 minutes at 0° C., then 1.2 ml of cold saturated sodium bicarbonate was added, the mixture stirred at 0° C. for 10 minutes, then at room temperature for 15 minutes, the volatiles removed and the residue taken up in ether and water. The ether layer was separated, washed with brine, dried and evaporated. The residual oil was flash chromatographed, eluting 40 ml fractions with hexane:ethyl acetate (2:1), giving from fractions 12–21, 600 mg of the desired compound.

EXAMPLE 44

2,5-Anhydro-1-deoxy-1-(diethoxyphsophinyl)-1-fluoro-2-C-[(phenylmethoxy)methyl]-3,4-bis-O-(phenylmethyl)-D-glucitol A solution of 992 mg of 2,5-anhydro-1-deoxy-1-(diethoxyphosphinyl)-1-fluoro-2-C-[(phenylmethoxy)methyl]-3,4-bis-0-(phenylmethyl)-D-glucitol, acetate in 3.4 ml of dry ethanol was treated with 3.76 μl of 2.3N sodium ethoxide in ethanol under argon. After 1 hour, 160 μl of glacial acetic acid was added, the volatiles removed and the residue worked up to give an oil. This oil was flash chromatographed, eluting 40 ml fractions with hexane:ethyl acetate (2:1), giving from fractions 9–18, 723 mg of the desired compound.

EXAMPLE 45

[1R(or 1S)]-2,5-Anhydro-1-deoxy-1-(diethoxyphosphinyl)-1-fluoro-2-C-[(phenylmethoxy)methyl-3,4-bis-O-(phenylmethyl)-D-glucitol, diphenyl phosphate A 726 mg portion of 2,5-anhydro-1-deoxy-1-(diethoxyphosphinyl)-1-fluoro-2-C-[(phenylmethoxy)methyl]-3,4-bis-O-(phenylmethyl)-D-glucitol was dissolved in 3.2 ml of pyridine, cooled in an ice bath, and 500 μl of diphenyl chlorophosphate added via a syringe. After I hour at 0° C. the mixture was refrigerated overnight, then warmed to room temperature and 300 μl of water added. After 20 minutes the volatiles were removed and the residue worked up to an oil. Flash chromatography, eluting 30 ml fractions with hexane:-ethyl acetate (3.2), gave from fractions 4–12, 880 mg of the desired compound.

EXAMPLE 46

2,5-Anhydro-1-deoxy-1-fluoro-2-(hydroxvmethyl)-1-phosphono-D-glucitol. 6-(dihydroqen phosphate)

A solution of 770 mg of [1R(or 1S)]-2,5-anhydro-1-deoxy-1-(diethoxyphosphinyl)-1-fluoro-2-C-[(phenylmethoxy)methyl]-3,4-bis-O-(phenylmethyl)-D-glucitol, diphenyl phosphate in 4 ml of deuterated chloroform was treated with 380 μl of trimethylsilyl bromide under argon. After 20 hours the volatiles were removed, 5 ml of acetone and 20 μl of water added and the mixture evaporated. This procedure was repeated twice, giving an oil. This oil was dissolved in 40 ml of methanol and hydrogenated over 10% palladium on carbon, giving a yellow oil. This oil was dissolved in 40 ml of methanol and hydrogenated over platinum oxide, giving 410 mg of the desired product as a colorless oil.

EXAMPLE 47

4,7-Anhydro-4-C-(benzoyloxy)methyl1-1,2,3-trideoxy-D-manno-octa-1,2-dienitol, tribenzoate To a stirred solution of 31.5 g of D-fructofuranose, pentabenzoate [P. Brigl and W. Schinle, Ber., 66, 325–330 (1933)], 16.8 g of propargyltrimethylsilane and 675 ml of acetonitrile at 0° C. was added 6.36 ml of boron trifluoride etherate during 2 minutes. The mixture was stirred at 25° C. for 48 hours and then partitioned with ethyl acetate:hexane (2:1) and aqueous sodium bicarbonate. The organic layer was separated, washed with water and brine, dried and concentrated to a gum. The gum was subjected to column chromatography on silica gel, eluting with heptane:ethyl acetate, giving the desired compound as a syrup; CMR δ 208 (C=C=C).

EXAMPLE 48

4,7-Anhydro-1,2,3-trideoxy-4-C-(hydroxymethyl)-D-gluco(or D-manno)-octa-1,2-dienitol A suspension of 19.6 g of 4,7-anhydro-4-C-[(benzoyloxy)methyl]-1,2,3-trideoxy-D-manno-octa-1,2-dienitol, tribenzoate in 320 ml of 0.5M sodium methoxide in methanol was stirred at 25° C. for 4 hours and then treated with 100 ml of Dowex ® 50W (H+) ion exchange resin. The mixture was filtered, the filtrate concentrated and the residue partitioned with petroleum ether and water. The aqueous phase was evaporated, giving the desired compound as a syrup; pair of spots on TLC [ethyl acetate:methanol (50:1)] for anomeric mixture, Rf=0.25 and 0.30.

EXAMPLE 49

4,7:4¹,5-Dianhydro-1,2,3-trideoxy-4-C-[(1-hydroxy-1-methylethoxy)methyl]-D-manno-octa-1,2-dienitol To a stirred mixture of 23 g of 4,7-anhydro-1,2,3-trideoxy-4-C-(hydroxymethyl)-D-gluco (or D-manno)-octa-1,2-dienitol, 56 g of anhydrous cupric sulfate and 1220 ml of acetone, was added dropwise 2.0 ml of concentrated sulfuric acid. The mixture was stirred at 25° C. for 3 days, then cooled to 0° C. and filtered into a flask containing 11 ml of pyridine and 14 g of sodium carbonate. The mixture was stirred until the solution phase was neutralized and then filtered. The filtrate was concentrated and the residue subjected to column chromatography on silica gel, eluting with ethyl acetate:methanol, giving the desired compound as a light yellow syrup; PMR δ 1.38 and 1.43 (each 3H, s, CH$_3$).

EXAMPLE 50

4,7:4¹,5-Dianhydro-1,2,3-trideoxy-4-C-[(1-hydroxy-1-methylethoxy)methyl]-6,8-bis-O-(phenylmethyl)-D-manno-octa-1,2-dienitol To a stirred mixture of 7.2 g of washed 50% sodium hydride and 25 ml of dimethylformamide was added a solution of 12.1 g of 4,7:4¹,5-dianhydro-1,2,3-trideoxy-4-C-[(1-hydroxy-1-methylethoxy)methyl]-D-manno-octa-1,2-dienitol in 55 ml of dimethylformamide at 0° C. The resulting mixture was treated with 29.7 ml of benzyl bromide during 15 minutes, then stirred at 25° C. for 24 hours, cooled to 0° C. and treated dropwise with 8 ml of methanol. After stirring for 20 minutes at 25° C., the volatiles were removed in vacuo at 50° C. The residue was partitioned with dichloromethane and water. The organic layer was washed with water, dried and concentrated. The residue was column chromatographed on silica gel, eluting with heptane:ethyl acetate, giving the desired product as an oil; PMR δ 4.55 (3H,s) and 4.59 (3H,dd).

EXAMPLE 51

2,5:2¹,3-Dianhydro-2-C-(1-hydroxy-1-methylethoxy)-methyl-4,6-bis-O-(phenylmethyl)-D-mannose A solution of 4.3 g of 4,7:4¹$^{pb}$,⁵-dianhydro-1,2,3-trideoxy-4-C-[(1-hydroxy-1-methylethoxy)methyl]-6,8-bis-O-(phenylmethyl)-D-manno-octa-1,2-dienitol and 1.0 ml of pyridine in 100 ml of dichloromethane at −78° C. was ozonized for 45 minutes, then purged free of ozone and treated successively with 5.1 g of zinc dust and 10 ml of acetic acid. The stirred mixture was warmed to 25° C. and partitioned with hexane:ether (2:1) and water. The organic layer was washed successively with water, sodium bicarbonate solution, water and brine, then dried and concentrated, giving the desired compound as an oil; PMR δ 9.7 (O=CH).

EXAMPLE 52

2,5-Anhydro-2-C-(diethoxyphosphinyl)hydroxymethyl-1.3-O-(1-methylethylidene)-4,6-bis-O-(phenylmethyl)-D-glucitol To a stirred solution of 4.1 g of 2,5:2¹,-3-dianhydro-2-C-[(1-hydroxy-1-methylethoxy)methyl]-4,6-bis-O-(phenylmethyl)-D-mannose in 6.5 ml of diethyl phosphite at 25° C., was added 1.5 ml of 1.5M sodium ethoxide in ethanol. After 16 hours at 25° C. the solution was treated with 0.5 ml of 4M sodium dihydrogen phosphate and diluted with dichloromethane. The solution was dried, filtered and concentrated at 0.05 mm mercury and 35° C.. The residue was column chromatographed on silica gel, eluting with hexane:ethyl acetate to give the title compounds as an epimeric mixture.

Polar epimer: m.p. 68°–70° C. (from petroleum ether-ethyl acetate)

Mobile epimer: syrup; PMR δ 1.3 (CH$_3$CH$_2$-).

EXAMPLE 53

2,5-Anhydro-2-C-[(diethoxyphosphinyl)[[2-(trimethylsilyl)ethoxy]methoxy]methyl]-1,3-O-(1-methylethylidene)-4,6-bis-O-(phenylmethyl)-D-glucitol To a stirred solution of 1.0 g of 2,5-anhydro-2-C-[(diethoxyphosphinyl)hydroxymethyl]-1,3-O-(1-methylethylidene)-4,6-bis-O-(phenylmethyl)-D-glucitol in 15 ml of dichloromethane was added 1.6 ml of diisopropylethylamine followed by 1.0 ml of 2-(trimethylsilyl)ethoxymethyl chloride. The mixture was stirred at 45° C. for 48 hours, then cooled and treated with water. The solvents were evaporated and the residue purified by chromatography on silica gel, giving the desired compound as an oil; PMR δ 0.01 (s, (CH$_3$).

EXAMPLE 54

2,5-Anhydro-2-C-[(diethoxyphosphinyl)[[2-(trimethylsilyl)ethoxy]methoxy]methyl]-1,3-O-(1-methylethylidene)-D-glucitol A solution of 1.0 g of 2,5-anhydro-2-C-[(diethoxyphosphinyl)[[2-(trimethylsilyl)ethoxy]methoxy]methyl]-1,3-O-(1-methylethylidene)-4,6-bis-O-(phenylmethyl)-D-glucitol in methanol was hydrogenated in the presence of 0.5 g of palladium hydroxide on carbon at 52 psi for 16 hours. The mixture was filtered and the filtrate concentrated. The residue was column chromatographed on silica gel giving the desired compound as an oil; PMR δ 0.01 (s, (CH$_3$)$_3$Si.

EXAMPLE 55

2,5-Anhydro-2-C-[(diethoxyphsophinyl)[[2-(trimethylsilyl)ethoxy]methoxy]methoxy -1,3-O-(1-methylethylidene)-D-glucitol, 6-(diphenyl phosphate)

To a stirred solution of 2,5-anhydro-2-C-[(diethoxyphosphinyl)[[2-(trimethylsilyl)ethoxy]methoxy]methyl]-1,3-O-(1-methylethylidene)-D-glucitol in 2 ml of pyridine at 0° C. was added 0.15 ml of diphenyl phosphorochloridate. After 2 hours the solution was treated with water at 25° C. and then partitioned with ether and water. The ether layer provided a residue which was chromatographed on silica gel, giving the desired compound as an oil; CMR δ 69.1 (d, COP, J=7.0 Hz).

EXAMPLE 56

2,5-Anhydro-2-C-(hydroxyphosphonomethyl)-D-glucitol, 6-(dihydrogen phosphate)

To a solution of 75 mg of 2,5-anhydro-2-C-[(diethoxyphosphinyl)[[2-(trimethylsilyl)ethoxy]methoxy]methyl]-1,3-O-(1-methylethylidene)-D-glucitol, 6-(diphenyl phosphate) in 0.5 ml of dichloromethane was added 0.05 ml of bromotrimethylsilane. After 5 hours the solution was diluted with aqueous acetone and then concentrated. The residue was dissolved in 10 ml of ethanol and hydrogenated in the presence of 50 mg of platinum oxide at 50 psi for 4 hours. After filtration the filtrate was evaporated and the residue partitioned with ethyl acetate and water. The aqueous phase was concentrated to give the desired product as a syrup; CMR $\delta$ 66.1 (d, COP, J=3.3 HZ) and (d, HOCP, J=1.57Hz).

EXAMPLE 57

2,5-Anhydro-2-C-[(diethoxyphosphinyl)fluoromethyl]-1,3-O-(1-methylethylidene)-4,6-bis-O-(phenylmethyl)-D-glucitol To a stirred solution of 1.0 g of 2,5-anhydro-2-C-[(diethoxyphosphinyl)hydroxymethyl]-1,3-O-(1-methylethylidene)-4,6-bis-O-(phenylmethyl)-D-glucitol in 10 ml of dichloromethane at 0° C. was added 0.6 ml of diethylaminosulfur trifluoride. The reaction mixture was stirred at 20° C. for 3 hours, then diluted with dichloromethane and treated with sodium bicarbonate solution. The organic layer was washed with water, dried and concentrated. The residue was subjected to column chromatography on silica gel, eluting with hexane:ethyl acetate, giving the more mobil component as an oil; CMR $\delta$ 86.6 (dd, FCP).

EXAMPLE 58

2,5-Anhydro-2-C-[(diethoxyphsophinyl)fluoromethyl]-1,3-O-(1-methylethylidene)-D-glucitol A mixture of 0.17 g of 2,5-anhydro-2-C-[(diethoxyphosphinyl)fluoromethyl]-1,3-O-(1-methylethylidene)-4,6-bis-O-(phenylmethyl)-D-glucitol and 0.2 g of Raney nickel in 10 ml of ethanol was refluxed for 5 minutes, then cooled and filtered. The filtrate was hydrogenated at 45 psi in the presence of 0.2 g of palladium hydroxide for 6 hours. The mixture was filtered and the filtrate concentrated, giving the desired compound as a syrup; CMR $\delta$ 86.6 (dd, FCP, J=167 and 191 Hz).

EXAMPLE 59

2,5-Anhydro-2-C-[(diethoxyphsophinyl)fluoromethyl]-1,3-O-(1-methylethylidene)-D-glucitol, 6-(diphenyl phosphate)

To a stirred solution of 50 mg of 2,5-anhydro-2-C-[(diethoxyphosphinyl)fluoromethyl]-1,3-0-(1-methylethylidene)-D-glucitol in 1 ml of pyridine at O° C. was added 0.04 ml of diphenyl phosphorochloridate. The reaction proceeded as described in Example 54, giving the desired compound as an oil; CMR $\delta$ 68.8 (d, COP, J=5.6 Hz).

EXAMPLE 60

2,5-Anhydro-2-C-(fluorophosphonomethyl)-D-glucitol, 6-(dihydrogen phosphate)

As described in Example 56, treatment of 2,5-anhydro-2-C-[(diethoxyphosphinyl)fluoromethyl]-1,3-O-(1-methylethylidene)-D-glucitol, 6-(diphenyl phosphate) with bromotrimethylsilane in dichloromethane, followed by hydrogenation in the presence of platinum oxide in ethanol, gave the desired product as a syrup; CMR $\delta$ 62.1 (d, COP, J=4.4 Hz) and 91.4 (dd, FCP, J=153 and 179 Hz).

EXAMPLE 61

1-Deoxy-1-(diethoxyphosphinyl)-1,1-difluoro-3,4,6-tris-O-(phenylmethyl)-D-fructofuranose In accordance with M. Obayashi et al., *Tetrahedron Letters*, 2323-2326 (1982), to a solution of lithium diisopropylamide (prepared from 17.2 ml of 1.6M n-butyllithium in hexane and 2.78 g of diisopropylamine in 50 ml of tetrahydrofuran) at −78° C., was added a solution of 4.70 g of diethyl difluoromethylphosphonate in 10 ml of tetrahydrofuran during 10 minutes, thereby forming (diethylphosphinyl)difluoromethyllithium. After 15 minutes, a solution of 2,3,5-tris-O-(phenylmethyl)-D-arabinonic acid, gamma-lactone [Y. Rabinsohn & H. G. Fletcher, *J. Org. Chem.*, 32, 3452-3457 minutes. The solution was stirred at −78° C. for 1 hour, warmed to −15° C. during 15 minutes, recooled to −78° C. and treated with 3 ml of glacial acetic acid. The mixture was partitioned with ether and water. The ether layer was washed with water, sodium bicarbonate solution and brine, dried and concentrated. The residue was subjected to column chromatography on silica gel (heptane-ethyl acetate) giving the desired compound as an oil; CMR $\delta$ 100.7 (major anomer) and 104.0 (minor anomer); (multiplets, anomeric carbon atom).

EXAMPLE 62

1-Deoxy-1-(diethoxyphosphinyl)-1,1-difluoro-3,4,6-tris-O-(phenylmethyl)-D-fructofuranosyl chloride To a stirred solution of 14.4 g of 1-deoxy-1-(diethoxyphosphinyl)-1,1-difluoro-3,4,6-tris-O-(phenylmethyl)-D-fructofuranose in 50 ml of dichloromethane was added 7.3 ml of thionyl chloride and several drops of dimethylformamide. The solution was stirred at 25° C. for 16 hours, then diluted with ether and treated with icewater. The ether layer was washed with sodium bicarbonate solution, water and brine, dried and concentrated. The residue was subjected to column chromatography on silica gel, giving the desired compound as an oil, CMR $\delta$ 105.1 (multiplet, anomeric carbon atom).

EXAMPLE 63

2,5-Anhydro-1-deoxy-1-(diethoxyphsophinyl)-1,1-difluoro-3,4,6-tris-O-(phenylmethyl)-D-mannitol A solution of 1.56 g of 1-deoxy-1-(diethoxyphosphinyl)-1,1-difluoro-3,4,6-tris-O-(phenylmethyl)-D-fructofuranosyl chloride, 4 ml of tributyltin hydride, 50 mg of azobisisobutyronitrile and 25 ml of toluene was stirred and refluxed for 90 minutes. The toluene was evaporated and the residue partitioned with acetonitrile-hexane. The acetonitrile solution was concentrated and the residue subjected to column chromatography on silica gel, giving the more mobile component as an oil, CMR $\delta$ 82.2 (doublet of triplets, O-C-CF$_2$P).

EXAMPLE 64

2,5-Anhydro-1-deoxy-1-(diethoxyphosphinyl)-1,1-difluoro-3,4-bis-O-(phenylmethyl)-D-mannitol, acetate To a stirred solution of 1.04 g of 2,5-anhydro-1-deoxy-1-(diethoxyphosphinyl)-1,1-difluoro-3,4,6-tris-O-(phenylmethyl)-D-mannitol in 5.3 ml of acetic anhydride at 0° C., was added 0.11 ml of boron trifluoride etherate. After 90 minutes at 0° C. the solution was diluted with ether and stirred with sodium bicarbonate solution for 5 minutes. The organic layer was washed with water and brine, dried and concentrated. The residue was subjected to column chromatography on silica gel (heptane-ethyl acetate), giving the desired compound as an oil, PMR $\delta$ 2.00 (singlet, acetyl group).

EXAMPLE 65

2,5-Anhydro-1-deoxy-1-(diethoxyphosphinyl)-1,1-difluoro-3,4-bis-O-(phenylmethyl)-D-mannitol To a stirred solution of 0.54 g of 2,5-anhydro-1-deoxy-1-(diethoxyphosphinyl)-1,1-difluoro-3,4-bis-O-(phenylmethyl)-D-mannitol, acetate in 3.0 ml of ethanol was added 0.56 ml of 1.8M sodium ethoxide in ethanol at 25° C. After 2 hours the solution was treated with 0.12 ml of acetic acid and diluted with ether. The solution was washed with water, sodium bicarbonate solution and brine, dried and concentrated. The residue was subjected to column chromatography on silica gel, giving the desired compound as an oil, CMR $\delta$ 61.8 ($CH_2OH$).

EXAMPLE 66

2,5-Anhydro-1-deoxy-1-(diethoxyphosphinyl)-1,1-difluoro-3,4-bis-O-(phenylmethyl)-D-mannitol, 6-(diphenyl phosphate)

To a stirred solution of 0.14 g of 2,5-anhydro-1-deoxy-1-(diethoxyphosphinyl)-1,1-difluoro-3,4-bis-O-(phenylmethyl)-D-mannitol in 0.84 ml of pyridine at 0° C., is added 0.12 ml of diphenylphosphoryl chloride. This mixture is stirred at 25° C. for 3 hours, treated with 0.25 ml of water, stirred at 25° C. for 45 minutes and then partitioned with ether-water. The ether layer is washed with water and brine, dried and concentrated. The residue is subjected to chromatography on silica gel (heptane-ethyl acetate), giving the desired compound as a syrup, TLC [ethyl acetate:heptane:acetic acid (30:20:1)] Rf=0.60.

EXAMPLE 67

2,5-Anhydro-1-deoxy-1,1-difluoro-1-phosphono-D-mannitol, 6-(dihydrogen phosphate)

To a stirred solution of 183 mg of 2,5-anhydro-1-deoxy-1-(diethoxyphosphinyl)-1,1-difluoro-3,4-bis-O-(phenylmethyl)-D-mannitol, 6-(diphenyl phosphate) in 0.5 ml of dichloromethane at 0° C., was added 0.2 ml of bromotrimethylsilane. The solution was stirred at 25° C. for 20 hours and then diluted with 15 ml of acetone:-water (50:1). After 30 minutes the solution was concentrated to a syrup. This syrup was dissolved in 20 ml of methanol and hydrogenated on a Parr shaker at 25° C. and 58 psi in the presence of 75 mg of 10% palladium on carbon for 20 hours. The catalyst was removed by filtration and the filtrate concentrated to a syrup. This syrup was dissolved in 20 ml of methanol and hydrogenated on a Parr shaker at 25° C. and 56 psi in the presence of 40 mg of platinum oxide for 5 hours. The catalyst was removed by filtration and the filtrate concentrated. The residue was dissolved in water, filtered and concentrated, giving the desired product as a syrup, CMR $\delta$ 65.8 (COP, J=2.7Hz) and 120.0 ($CF_2P$, J=262 and 192 Hz).

EXAMPLE 68

2,5-Anhydro-1-deoxy-1-(diethoxyphosphinyl)-1,1-difluoro-3,4,6-tris-O-(phenylmethyl)-D-glucitol Following the procedure of Example 63, reduction of 1-deoxy-1-(diethoxyphosphinyl)-1,1-difluoro-3,4,6-tris-O-(phenylmethyl)-D-fructofuranosyl chloride with tributyltin hydride, followed by column chromatography of the crude product gave the desired compound, the more polar component, as an oil, CMR $\delta$ 77.9 (doublet of triplets, O-C-$CF_2$P).

EXAMPLE 69

2,5-Anhydro-1-deoxy-1-(diethoxyphosphinyl)-1,1-difluoro-3,4-bis-O-(phenylmethyl)-D-glucitol, acetate Following the procedure of Example 64, treatment of 2,5-anhydro-1-deoxy-1-(diethoxyphosphinyl)-1,1-difluoro-3,4,6-tris-O-(phenylmethyl)-D-glucitol with boron trifluoride etherate and acetic anhydride gives the desired product.

EXAMPLE 70

2,5-Anhydro-1-deoxy-1-(diethoxyphsophinyl)-1,1-difluoro-3,4-bis-O-(phenylmethyl)-D-glucitol Following the procedure of Example 65, treatment of 2,5-anhydro-1-deoxy-1-(diethoxyphosphinyl)-1,1-difluoro-3,4-bis-0-(phenylmethyl)-D-glucitol, acetate with sodium ethoxide in ethanol gives the desired compound.

EXAMPLE 71

2,5-Anhydro-1-deoxy-1-(diethoxyphosphinyl)-1,1-difluoro-3,4-bis-0-(phenylmethyl)-D-glucitol, 6-(diphenyl phosphate)

Following the procedure of Example 66, treatment of 2,5-anhydro-1-deoxy-1-(diethoxyphosphinyl)-1,1 -difluoro-3,4-bis-0-(phenylmethyl)-D-glucitol with diphenylphosphoryl chloride in pyridine gives the desired compound.

EXAMPLE 72

2,5-Anhydro-1-deoxy-1,1-difluoro-1-phosphono-D-glucitol, 6-(dihydrogen phosphate)

Following the procedure of Example 67, treatment of 2,5-anhydro-1-deoxy-1-(diethoxyphosphinyl)-1,1-difluoro-3,4-bis-O-(phenylmethyl)-D-glucitol, 6-(diphenyl phosphate) with bromotrimethylsilane, followed by hydrogenation first over palladium on carbon and then platinum gives the desired product.

EXAMPLE 73

1-Deoxy-1-(diethoxyphosphinyl)-1,1-difluoro-3,4-bis-O-(phenylmethyl)-D-fructofuranose, 2,6-diacetate To a stirred solution of 6.06 g of 1-deoxy-1-(diethoxyphosphinyl)-1,1-difluoro-3,4,6-tris-O-(phenylmethyl)-D-fructofuranose in 20 ml of acetic anhydride at 0° C. was added dropwise, 2.46 ml of boron trifluoride etherate. After 45 minutes at 0° C., the solution was diluted with ether and stirred at 0° C. for 5 minutes with 50 ml of saturated sodium bicarbonate. The ether layer was washed with water and brine, dried and concentrated. The residue was subjected to column chromatography on silica gel, giving the desired compound as an oil; CMR $\delta$ 20.7 and 21.6 (singlets) and 167.5 and 170.4 (singlets), corresponding to $CH_3$ and C=O respectively, of the acetyl groups.

EXAMPLE 74

1-Deoxy-1-(diethoxyphosphinvl)-1 1-difluoro-3,4-bis-O-(phenylmethyl)-D-fructofuranose To a solution of 0.84 g of 1-deoxy-1-(diethoxyphosphinyl)-1,1-difluoro-3,4-bis-0-(phenylmethyl)-D-fructofuranose, 2,6-diacetate in 3.0 ml of ethanol was added 1.0 ml of a 1.5M solution of sodium ethoxide in ethanol at 25° C. After 24 hours the solution was treated with 0.06 ml of glacial acetic acid and evaporated to dryness. The residue was partitioned with ether and water. The ether layer was concentrated and the residue subjected to column chromatography on silica gel, giving the desired product as an oil, CMR δ 100.5 (doublet of triplets, anomeric carbon).

EXAMPLE 75

1-Deoxy-1-(diethoxyphsophinyl)-1,1-difluoro-3 4-bis-O-(phenylmethyl)-D-fructofuranose, 6-(diphenyl phosphate)

To a stirred solution of 0.38 g of 1-deoxy-1-(diethoxyphosphinyl)-1,1-difluoro-3,4-bis-O-(phenylmethyl)-D-fructofuranose in 2.2 ml of pyridine at 0° C., was added 0.21 ml of diphenylphosphoryl chloride. After 20 hours at 0° C., the mixture was treated with 0.4 ml of water, then stirred at 25° C. for 45 minutes and partitioned with ether-water. The ether layer was washed with water and brine, dried and concentrated. The residue was subjected to chromatography on silica gel, giving the desired product as an oil, CMR δ 68.2 [doublet, J=5.7 Hz, $CH_2OPO(OC_6H_5)_2$].

EXAMPLE 76

2-Trimethylsilyl-1-deoxy-1-(diethoxyphosphinyl)-1,1-difluoro-3,4-bis-O-(phenylmethyl)-D-fructofuranoside. 6-(diphenyl phosphate)

To a stirred solution of 2.18 g of 1-deoxy-1-(diethoxyphosphinyl)-1,1-difluoro-3,4-bis-O-(phenylmethyl)-D-fructofuranose, 6-(diphenyl phosphate) in 5.8 ml of toluene was added 2.9 ml of N,O-bis(trimethylsilyl)acetamide. After 2 hours at 25° C., the solution was evaporated at 40° C. under vacuum. The residue was partitioned with hexane:ether (5:1) and water at 0° C. The organic layer was dried and concentrated The residue was subjected to column chromatography on silica gel (heptane-ethyl acetate) giving the desired compound as an oil CMR δ 1.71 ($CH_3Si$) and 102.8 (anomeric carbon).

EXAMPLE 77

1-Deoxy-1,1-difluoro-1-phosphono-D-fructofuranose, 6-(dihydrogen phosphate)

Following the procedure of Example 67, 2-trimethylsilyl-1-deoxy-1-(diethoxyphosphinyl)-1,1-difluoro-3,4-bis-O-(phenylmethyl)-D-fructofuranoside, 6-(diphenyl phosphate) is treated with bromotrimethylsilane in dichloromethane, then hydrogenated first over palladium on carbon, and then over platinum, giving the desired product.

We claim:

1. A compound selected from those of the formula:

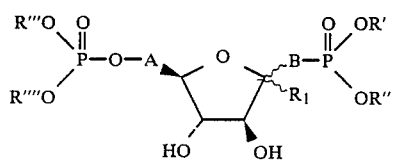

wherein A is selected from the group consisting of $C_1$-$C_4$ alkylene and $C_2$ to $C_4$ hydroxyalkylene; B is selected from the group consisting of $C_1$ to $C_4$ alkylene and $C_2$ to $C_4$ hydroxyalkylene in which the carbon atom of the alkylene moiety or the hydroxyalkylene moiety which is adjacent to the phosphorous atom is mono- or disubstituted with a substituent selected from the group consisting of halogen, hydroxy, and $C_1$ to $C_4$ alkoxy; $R_1$ is selected from the group consisting of hydrogen, $C_1$ to $C_4$ alkyl, $C_1$ to $C_4$ hydroxyalkyl, $C_2$ to $C_4$ dihydroxyalkyl, $C_3$ or $C_4$ trihydroxyalkyl and $C_4$ tetrahydroxyalkyl; R', R'', R''' and R'''' are selected independently from the group consisting of hydrogen, $C_1$ to $C_{18}$ alkyl, $C_3$ to $C_6$ cycloalkyl, phenyl, $C_3$ to $C_8$ isoalkyl, $Cl_3CCH_2$—, $CH_2CH=CH_2$—, $ZCH_2CHh_2$— [where Z is $SO_2R_2$, $SR_2$, $OR_2$, or $Si(R_2)_3$, and $R_2$ is $C_1$ to $C_3$ alkyl],

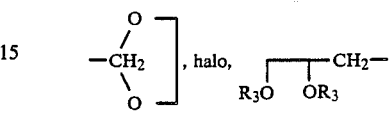

[where $R_3$ is $C_1$ to $C_3$ alkyl and $R_3$-$R_3$ is alkylene or acetal],

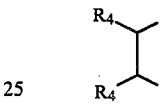

(where $R_4$ is hydrogen or methyl),

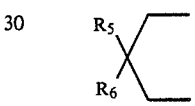

[where, when $R_5$=$R_6$, they are both hydrogen, fluoro or $C_1$-$C_4$ alkyl, $R_5$ is hydrogen, $R_6$ is fluoro, oxy or $OR_7$ [where $R_7$ is $C_1$ to $C_6$ alkyl, $C_3$ to $C_6$ cycloalkyl or aryl]],

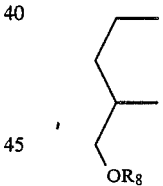

[where $R_8$ is hydrogen or $C_1$ to $C_{18}$ alkyl],

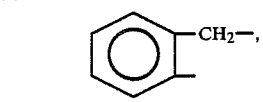

phenylmethyl, substituted phenylmethyl wherein the substituents are selected from $C_1$ to $C_{18}$ alkyl, $C_1$ to $C_6$ alkoxy, $NO_2$ and halogen, and mono- and disubstituted phenyl wherein the substituents are selected from $C_1$ to $C_{18}$ alkyl, $C_1$ to $C_6$ alkoxy, $NO_2$ and halogen; and, when any one or more of R', R'', R''' or R'''' are hydrogen, the pharmacologically acceptable salts thereof.

2. The compound according to claim 1, 3,6-anhydro-1,2-dideoxy-1-(diethoxyphosphinyl)-1,1-difluoro-D-manno-heptitol, 7-(diphenyl phosphate).

3. The compound according to claim 1, 3,6-anhydro-1,2-dideoxy-1,1-difluoro-1-phosphono-D-manno-heptitol, 7-(diphenyl phosphate).

4. The compound according to claim 1, [1R(and 1S)]-3,6-anhydro-1,2-dideoxy-1-(diethoxyphosphinyl)-1-fluoro-D-manno-heptitol, 7-(diphenyl phosphate).

5. The compound according to claim 1, (1R)-3,6-anhydro-1,2-dideoxy-1-fluoro-1-phosphono-D-manno-heptitol, 7-(diphenyl phosphate).

6. The compound according to claim 1, (1S)-3,6-anhydro-1,2-dideoxy-1-fluoro-1-phosphono-D-manno-heptitol, 7-(diphenyl phosphate).

7. The compound according to claim 1, 2,5-anhydro-1-deoxy-1-(diethoxyphosphinyl)-1-fluoro-D-glucitol 6-(diphenyl phosphate).

8. The compound according to claim 1, 2,5-anhydro-1-deoxy-1-(diethoxyphosphinyl)-1-fluoro-D-mannitol, 6-(diphenyl phosphate).

9. The compound according to claim 1, 2,5-deoxy-1-fluoro-1-phosphono-D-mannitol, 6-(diphenyl phosphate).

10. The compound according to claim 1, 3,6-anhydro-1,2-dideoxy-1,1-difluoro-1-phosphono-D-manno-heptitol 7-(dihydrogen phosphate).

11. The compound according to claim 1, (1R)-3,6-anhydro-1,2-dideoxy-1-fluoro-1-phosphono-D-mannoheptitol, 7-(dihydrogen phosphate).

12. The compound according to claim 1, (1S)3,6-anhydro-1,2-dideoxy-1-fluoro-1 -phosphono-D-mannoheptitol, 7-(dihydrogen phosphate).

13. The compound according to claim 1, 2,5-anhydro-1-deoxy-1-fluoro-1-phosphono-D-mannitol, 6-(dihydrogen phosphate).

14. The compound according to claim 1, 2,5-anhydro-1-deoxy-1-fluoro-1-phosphono-D-glucitol, 6-(dihydrogen phosphate).

15. The compound according to claim 1, 2,5-anhydro-1-deoxy-1-fluoro-2-(hydroxymethyl)-1-phosphono-D 6-(dihydrogen phosphate).

16. The compound according to claim 1, 2,5-2-(hydroxyphosphonomethyl)-D-glucitol, 6-(dihydro phosphate).

17. The compound according to claim 1, 2,5-2-C-(fluorophosphonomethyl)-D-glucitol, 6-(dihydrogen phosphate).

18. The compound according to claim 1, 2,5-anhydro-1-deoxy-1,1-difluoro-1-phosphono-D-mannitol, 6-(dihydrogen phosphate).

19. The compound according to claim 1, 2,5-anhydro-1-deoxy-1,1-difluoro-1-phosphono-D-glucitol, 6-(dihydrogen phosphate).

20. The compounds according to claim 1, [1R]-2,5-anhydro-1-C-(diethoxyphosphinyl)-D-mannitol, 6-(diphenyl phosphate), [1S]-2,5-anhydro-1-C-(diethoxyphosphinyl)-D-mannitol, 6-(diphenyl phosphate) and [1R(and 1S)]-2,5-anhydro-1C-(diethoxyphosphinyl)-D-mannitol, 6-(diphenyl phosphate).

21. The compounds according to claim 1, [1R]-2,5-anydro-1-C-phosphono-D-mannitol, 6-(diphenyl phosphate), [1S]-2,5-anhydro-1-C-phosphono-D-mannitol, 6-(diphenyl phosphate) and [1R(and 1S]-2,5-anhydro-1-C-phospohono-D-mannitol, 6-(diphenyl phosphate).

22. The compounds according to claim 1, [1R]-3,6-anhydro-2-deoxy-1-C-(diphenoxyphosphinyl)-D-manno-heptitol, 7-(diphenyl phosphate), [1S]-3,6-anhydro-2-deoxy-1-C-(diphenoxyphosphinyl)-D-manno-heptitol, 7-(diphenyl phosphate) and [1R(and 1S]-3,6-anhydro-2-deoxy-1C-(diphenoxyphosphinyl)-D-manno-heptitol, 7-(diphenyl phosphate).

23. The compounds according to claim 1, [1R]-2,5-anhydro-1-C-phosphono-D-mannitol, 6-(dihydrogen phosphate), [1S]-2,5-anhydro-1-C-phosphono-D-mannitol, 6-(dihydrogen phosphate) and [1R(and 1S)]-2,5-anhydro-1-C-phosphono-D-mannitol, 6-(dihydrogen phosphate).

24. The compounds according to claim 1, [1R]-3,6-anhydro-2-deoxy-1-phosphono-D-manno-heptitol, 7-(dihydrogen phosphate), [1S]-3,6-anhydro-2-deoxy-1-phosphono-D-mannoheptitol, 7-(dihydrogen phosphate) and [1R(and 1S)]-3,6-anhydro-2-deoxy-1-phosphono-D-manno-heptitol, 7-(dihydrogen phosphate).

25. A compound selected from those of the formula:

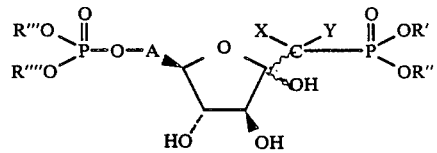

wherein A is selected from the group consisting of $C_1$ to $C_4$ alkylene and $C_2$ to $C_4$ hydroxyalkylene; R', R", R''' and R'''' are selected independently from the group consisting of hydrogen, $C_1$ to $C_{18}$ alkyl, $C_3$ to $C_6$ cycloalkyl, phenyl, $C_3$ to $C_8$ isoalkyl, $Cl_3CCH_2$—, $CH_2CH=CH_2$—, $ZCH_2CH_2$—, [where Z is $SO_2R_2$, $SR_2$, $OR_2$, or $Si(R_2)_3$, and $R_2$ is $C_1$–$C_3$ alkyl],

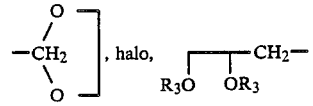

[where $R_3$ is $C_1$ to $C_3$ alkyl and $R_3$–$R_3$ is alkylene or acetal],

(where $R_4$ is hydrogen or methyl),

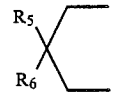

[where, when $R_5=R_6$ they are both hydrogen, fluoro or $C_1$–$C_4$ alkyl, $R_5$ is hydrogen, $R_6$ is fluoro, hydroxy or $OR_7$ [where $R_7$ is $C_1$–$C_6$ alkyl, $C_3$ to $C_6$ cycloalkyl or aryl]],

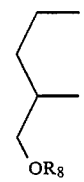

[where $R_8$ is hydrogen or $C_1$ to $C_{18}$ alkyl],

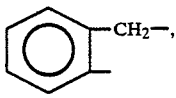

phenylmethyl, substituted phenylmethyl wherein the substituents are selected from $C_1$ to $C_{18}$ alkyl, $C_1$ to $C_6$ alkoxy, $NO_2$ and halogen and mono- and disubstituted phenyl wherein the substituents are selected from $C_1$ to $C_{18}$ alkyl, $C_1$ to $C_6$ alkoxy, $NO_2$ and halogen; X and Y are selected independently from the group consisting of hydrogen, halogen, hydroxy and $C_1$ to $C_4$ alkoxy; and, when any one or more of R', R", R'" or R"" are hydrogen, the pharmacologically acceptable salts thereof.

26. The compound according to claim 25, 1-deoxy-1,1-difluoro-1-phosphono-D-fructofuranose, 6-(dihydrogen phosphate).

27. A method of treating hyperglycemia in a mammal in need of such treatment which comprises administering to said mammal a therapeutically effective amount of a compound selected from those of claim 1 or claim 25.

28. A pharmaceutical composition of matter which comprises a therapeutically effective amount of a compound selected from those of claim 1 or claim 25 in association with a pharmaceutically acceptable carrier.

29. A method of treating diabetes in a mammal in need of such treatment which comprises administering to said mammal a therapeutically effective amount of a compound selected from those of claim 1 or claim 25.

* * * * *